(12) United States Patent
He et al.

(10) Patent No.: US 8,765,444 B2
(45) Date of Patent: Jul. 1, 2014

(54) COMPOSITIONS AND METHODS USING HERPES SIMPLEX VIRUS

(75) Inventors: Bin He, Chicago, IL (US); Dustin Verpooten, Schererville, IN (US); Yijie Ma, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 479 days.

(21) Appl. No.: 12/836,856

(22) Filed: Jul. 15, 2010

(65) Prior Publication Data

US 2011/0052630 A1    Mar. 3, 2011

Related U.S. Application Data

(60) Provisional application No. 61/225,710, filed on Jul. 15, 2009, provisional application No. 61/225,736, filed on Jul. 15, 2009.

(51) Int. Cl.
*C12N 7/00*    (2006.01)
*C12N 7/04*    (2006.01)
*A61K 39/245*    (2006.01)

(52) U.S. Cl.
USPC ............... 435/235.1; 435/236; 424/231.1

(58) Field of Classification Search
CPC ............... A61K 39/12; C12N 2710/16011; C12N 2710/16021; C12N 2710/16034; C12N 2710/16062; C12N 15/00
See application file for complete search history.

(56) References Cited

U.S. PATENT DOCUMENTS 5,585,096 A * 12/1996 Martuza et al. ............. 424/93.2
7,264,814 B2 * 9/2007 Nishiyama ................. 424/199.1

OTHER PUBLICATIONS

Chou et al., Science, 1990, 250:1262-1266.*
EMULSIGEN®-D Technical Bulletin, available from www.mvp-technologies.com/adjuvants/Emulsigen_D.pdf, 2 pages, copyright 2006.*

* cited by examiner

*Primary Examiner* — Stacy B. Chen
(74) *Attorney, Agent, or Firm* — Polsinelli PC; Teddy C. Scott, Jr.; Ron Galant

(57) ABSTRACT

Provided herein are methods and compositions for use in treating HSV-related conditions and diseases.

9 Claims, 14 Drawing Sheets

Figure 1
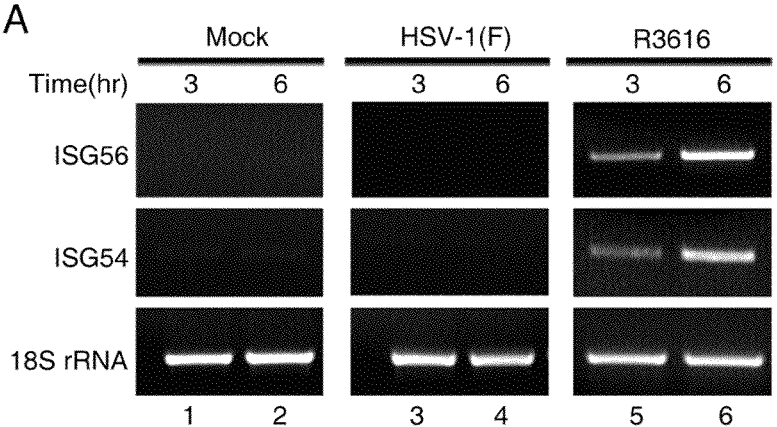
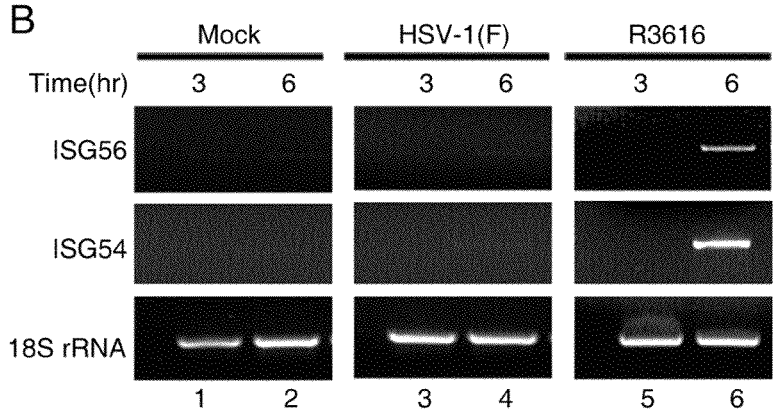
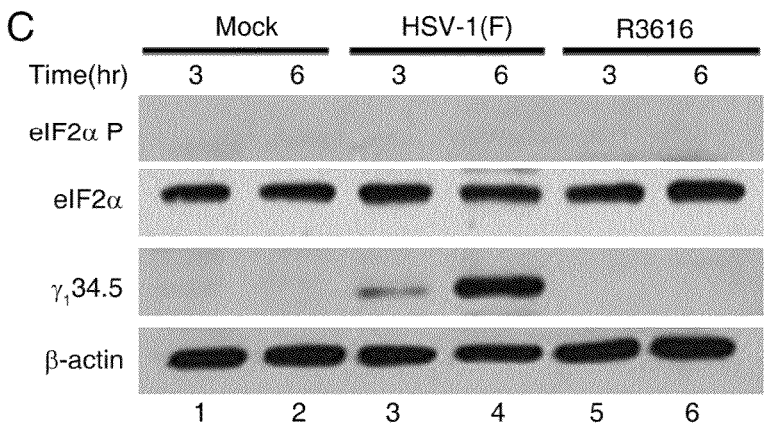

FIG. 12
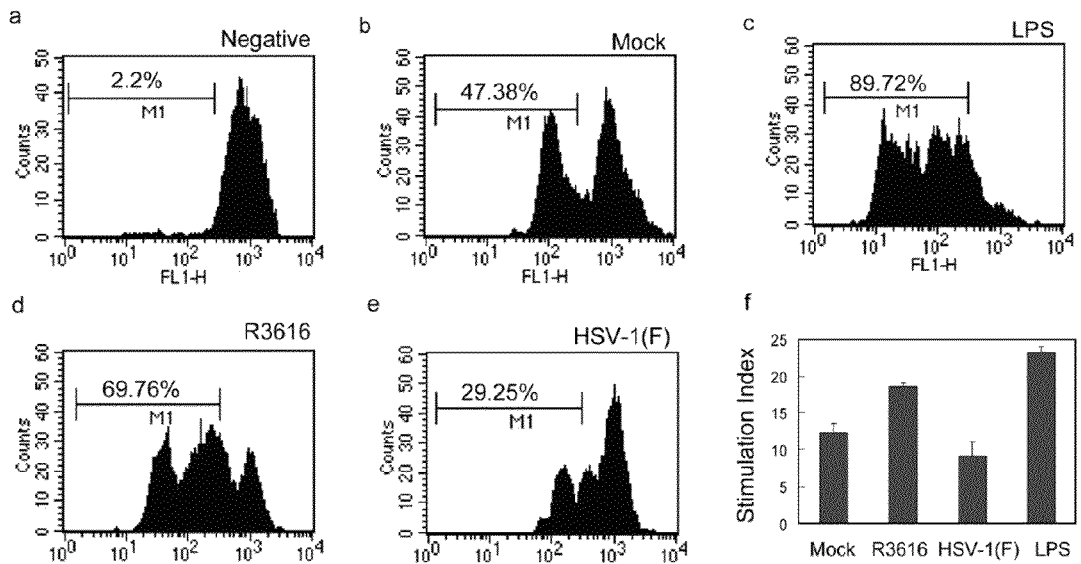
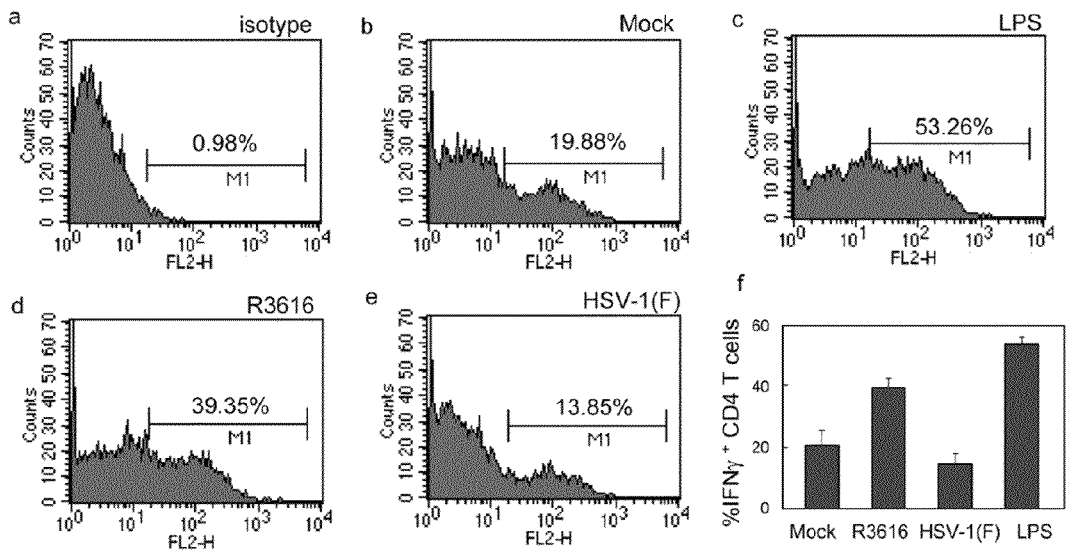

SEQUENCE LISTING

<160> NUMBER OF SEQ ID NOS: 22

<210> SEQ ID NO 1
<211> LENGTH: 729
<212> TYPE: PRT
<213> ORGANISM: Homo sapiens

<400> SEQUENCE: 1

```
Met Gln Ser Thr Ser Asn His Leu Trp Leu Leu Ser Asp Ile Leu Gly
1               5                   10                  15

Gln Gly Ala Thr Ala Asn Val Phe Arg Gly Arg His Lys Lys Thr Gly
            20                  25                  30

Asp Leu Phe Ala Ile Lys Val Phe Asn Asn Ile Ser Phe Leu Arg Pro
        35                  40                  45

Val Asp Val Gln Met Arg Glu Phe Glu Val Leu Lys Lys Leu Asn His
    50                  55                  60

Lys Asn Ile Val Lys Leu Phe Ala Ile Glu Glu Glu Thr Thr Thr Arg
65                  70                  75                  80

His Lys Val Leu Ile Met Glu Phe Cys Pro Cys Gly Ser Leu Tyr Thr
                85                  90                  95

Val Leu Glu Glu Pro Ser Asn Ala Tyr Gly Leu Pro Glu Ser Glu Phe
            100                 105                 110

Leu Ile Val Leu Arg Asp Val Gly Gly Met Asn His Leu Arg Glu
        115                 120                 125

Asn Gly Ile Val His Arg Asp Ile Lys Pro Gly Asn Ile Met Arg Val
    130                 135                 140

Ile Gly Glu Asp Gly Gln Ser Val Tyr Lys Leu Thr Asp Phe Gly Ala
145                 150                 155                 160

Ala Arg Glu Leu Glu Asp Asp Glu Gln Phe Val Ser Leu Tyr Gly Thr
                165                 170                 175

Glu Glu Tyr Leu His Pro Asp Met Tyr Glu Arg Ala Val Leu Arg Lys
            180                 185                 190

Asp His Gln Lys Lys Tyr Gly Ala Thr Val Asp Leu Trp Ser Ile Gly
        195                 200                 205

Val Thr Phe Tyr His Ala Ala Thr Gly Ser Leu Pro Phe Arg Pro Phe
    210                 215                 220

Glu Gly Pro Arg Arg Asn Lys Glu Val Met Tyr Lys Ile Ile Thr Gly
225                 230                 235                 240

Lys Pro Ser Gly Ala Ile Ser Gly Val Gln Lys Ala Glu Asn Gly Pro
                245                 250                 255

Ile Asp Trp Ser Gly Asp Met Pro Val Ser Cys Ser Leu Ser Arg Gly
            260                 265                 270

Leu Gln Val Leu Leu Thr Pro Val Leu Ala Asn Ile Leu Glu Ala Asp
        275                 280                 285

Gln Glu Lys Cys Trp Gly Phe Asp Gln Phe Phe Ala Glu Thr Ser Asp
    290                 295                 300

Ile Leu His Arg Met Val Ile His Val Phe Ser Leu Gln Gln Met Thr
305                 310                 315                 320

Ala His Lys Ile Tyr Ile His Ser Tyr Asn Thr Ala Thr Ile Phe His
                325                 330                 335

Glu Leu Val Tyr Lys Gln Thr Lys Ile Ile Ser Ser Asn Gln Glu Leu
            340                 345                 350

Ile Tyr Glu Gly Arg Arg Leu Val Leu Glu Pro Gly Arg Leu Ala Gln
        355                 360                 365
```

His Phe Pro Lys Thr Thr Glu Glu Asn Pro Ile Phe Val Val Ser Arg
370                 375                 380

Glu Pro Leu Asn Thr Ile Gly Leu Ile Tyr Glu Lys Ile Ser Leu Pro
385                 390                 395                 400

Lys Val His Pro Arg Tyr Asp Leu Asp Gly Asp Ala Ser Met Ala Lys
            405                 410                 415

Ala Ile Thr Gly Val Val Cys Tyr Ala Cys Arg Ile Ala Ser Thr Leu
            420                 425                 430

Leu Leu Tyr Gln Glu Leu Met Arg Lys Gly Ile Arg Trp Leu Ile Glu
        435                 440                 445

Leu Ile Lys Asp Asp Tyr Asn Glu Thr Val His Lys Lys Thr Glu Val
450                 455                 460

Val Ile Thr Leu Asp Phe Cys Ile Arg Asn Ile Glu Lys Thr Val Lys
465                 470                 475                 480

Val Tyr Glu Lys Leu Met Lys Ile Asn Leu Glu Ala Ala Glu Leu Gly
            485                 490                 495

Glu Ile Ser Asp Ile His Thr Lys Leu Leu Arg Leu Ser Ser Ser Gln
            500                 505                 510

Gly Thr Ile Glu Thr Ser Leu Gln Asp Ile Asp Ser Arg Leu Ser Pro
        515                 520                 525

Gly Gly Ser Leu Ala Asp Ala Trp Ala His Gln Glu Gly Thr His Pro
530                 535                 540

Lys Asp Arg Asn Val Glu Lys Leu Gln Val Leu Leu Asn Cys Met Thr
545                 550                 555                 560

Glu Ile Tyr Tyr Gln Phe Lys Lys Asp Lys Ala Glu Arg Arg Leu Ala
            565                 570                 575

Tyr Asn Glu Glu Gln Ile His Lys Phe Asp Lys Gln Lys Leu Tyr Tyr
            580                 585                 590

His Ala Thr Lys Ala Met Thr His Phe Thr Asp Glu Cys Val Lys Lys
        595                 600                 605

Tyr Glu Ala Phe Leu Asn Lys Ser Glu Glu Trp Ile Arg Lys Met Leu
610                 615                 620

His Leu Arg Lys Gln Leu Leu Ser Leu Thr Asn Gln Cys Phe Asp Ile
625                 630                 635                 640

Glu Glu Glu Val Ser Lys Tyr Gln Glu Tyr Thr Asn Glu Leu Gln Glu
            645                 650                 655

Thr Leu Pro Gln Lys Met Phe Thr Ala Ser Ser Gly Ile Lys His Thr
            660                 665                 670

Met Thr Pro Ile Tyr Pro Ser Ser Asn Thr Leu Val Glu Met Thr Leu
        675                 680                 685

Gly Met Lys Lys Leu Lys Glu Glu Met Glu Gly Val Val Lys Glu Leu
690                 695                 700

Ala Glu Asn Asn His Ile Leu Glu Arg Phe Gly Ser Leu Thr Met Asp
705                 710                 715                 720

Gly Gly Leu Arg Asn Val Asp Cys Leu
            725

<210> SEQ ID NO 2
<211> LENGTH: 2982
<212> TYPE: DNA
<213> ORGANISM: Homo sapiens

<400> SEQUENCE: 2
gccggcggtg gcgcggcgga gacccggctg gtataacaag aggattgcct gatccagcca    60

```
agatgcagag cacttctaat catctgtggc ttttatctga tattttaggc caaggagcta    120
ctgcaaatgt ctttcgtgga agacataaga aaactggtga tttatttgct atcaaagtat    180
ttaataacat aagcttcctt cgtccagtgg atgttcaaat gagagaattt gaagtgttga    240
aaaaactcaa tcacaaaaat attgtcaaat tatttgctat tgaagaggag acaacaacaa    300
gacataaagt acttattatg gaattttgtc catgtgggag tttatacact gttttagaag    360
aaccttctaa tgcctatgga ctaccagaat ctgaattctt aattgttttg cgagatgtgg    420
tgggtggaat gaatcatcta cgagagaatg gtatagtgca ccgtgatatc aagccaggaa    480
atatcatgcg tgttataggg gaagatggac agtctgtgta caaactcaca gatttggtg     540 cagctagaga attagaagat gatgagcagt ttgtttctct gtatggcaca gaagaatatt    600
tgcaccctga tatgtatgag agagcagtgc taagaaaaga tcatcagaag aaatatggag    660
caacagttga tctttggagc attggggtaa cattttacca tgcagctact ggatcactgc    720
catttagacc ctttgaaggg cctcgtagga ataagaagt gatgtataaa ataattacag     780
gaaagccttc tggtgcaata tctggagtac agaaagcaga aaatggacca attgactgga    840
gtggagacat gcctgtttct tgcagtcttt ctcggggtct tcaggttcta cttaccctg     900 ttcttgcaaa catccttgaa gcagatcagg aaaagtgttg gggttttgac cagttttttg    960
cagaaactag tgatatactt caccgaatgg taattcatgt ttttcgcta caacaaatga     1020 cagctcataa gatttatatt catagctata atactgctac tatatttcat gaactggtat    1080
ataaacaaac caaaattatt tcttcaaatc aagaacttat ctacgaaggg cgacgcttag    1140
tcttagaacc tggaaggctg gcacaacatt tccctaaaac tactgaggaa acccctatat    1200
ttgtagtaag ccgggaacct ctgaatacca taggattaat atatgaaaaa atttccctcc    1260
ctaaagtaca tccacgttat gatttagacg gggatgctag catggctaag gcaataacag    1320
gggttgtgtg ttatgcctgc agaattgcca gtaccttact gctttatcag gaattaatgc    1380
gaaaggggat acgatggctg attgaattaa ttaaagatga ttacaatgaa actgttcaca    1440
aaaagacaga agttgtgatc acattggatt tctgtatcag aaacattgaa aaaactgtga    1500
aagtatatga aaagttgatg aagatcaacc tggaagcggc agagttaggt gaaatttcag    1560
acatacacac caaattgttg agactttcca gttctcaggg aacaatagaa accagtcttc    1620
aggatatcga cagcagatta tctccaggtg gatcactggc agacgcatgg gcacatcaag    1680
aaggcactca tccgaaagac agaaatgtag aaaaactaca agtcctgtta aattgcatga    1740
cagagattta ctatcagttc aaaaaagaca aagcagaacg tagattagct tataatgaag    1800
aacaaatcca caaatttgat aagcaaaaac tgtattacca tgccacaaaa gctatgacgc    1860 acttacaga tgaatgtgtt aaaaagtatg aggcattttt gaataagtca gaagaatgga    1920
taagaaagat gcttcatctt aggaaacagt tattatcgct gactaatcag tgttttgata    1980
ttgaagaaga agtatcaaaa tatcaagaat atactaatga gttacaagaa actctgcctc    2040
agaaaatgtt tacagcttcc agtggaatca aacataccat gaccccaatt tatccaagtt    2100
ctaacacatt agtagaaatg actcttggta tgaagaaatt aaaggaagag atggaagggg    2160
tggttaaaga acttgctgaa aataaccaca ttttagaaag gtttggctct ttaaccatgg    2220
atggtggcct tcgcaacgtt gactgtcttt agcttctaa tagaagtttaa agaaagttt     2280 ccgtttgcac aagaaaataa cgcttgggca ttaaatgaat gcctttatag atagtcactt    2340
gtttctacaa ttcagtattt gatgtggtcg tgtaaatatg tacaatattg taaatacata    2400
aaaaatatac aaattttttgg ctgctgtgaa gatgtaattt tatcttttaa catttataat   2460
```

-continued

```
tatatgagga aatttgacct cagtgatcac gagaagaaag ccatgaccga ccaatatgtt    2520
gacatactga tcctctactc tgagtggggc taaataagtt attttctctg accgcctact    2580
ggaaatattt ttaagtggaa ccaaaatagg catccttaca aatcaggaag actgacttga    2640
cacgtttgta aatggtagaa cggtggctac tgtgagtggg gagcagaacc gcaccactgt    2700
tatactggga taacaatttt tttgagaagg ataaagtggc attatttat tttacaaggt    2760 gcccagatcc cagttatcct tgtatccatg taatttcaga tgaattatta agcaaacatt    2820
ttaaagtgaa ttcattatta aaaactattc attttttcc tttggccata aatgtgtaat    2880
tgtcattaaa attctaaggt catttcaact gttttaagct gtatatttct ttaattctgc    2940
ttactatttc atggaaaaaa ataaatttct caattttaat gt                       2982
```

<210> SEQ ID NO 3
<211> LENGTH: 263
<212> TYPE: PRT
<213> ORGANISM: Herpes simplex virus 1

<400> SEQUENCE: 3

```
Met Ala Arg Arg Arg His Arg Gly Pro Arg Arg Pro Arg Pro Pro
1               5                   10                  15

Gly Pro Thr Gly Ala Val Pro Thr Ala Gln Ser Gln Val Thr Ser Thr
                20                  25                  30

Pro Asn Ser Glu Pro Ala Val Arg Ser Ala Pro Ala Ala Pro Pro
            35                  40                  45

Pro Pro Pro Ala Ser Gly Pro Pro Ser Cys Ser Leu Leu Arg
    50                  55                  60

Gln Trp Leu His Val Pro Glu Ser Ala Ser Asp Asp Asp Asp Asp
65              70                  75                  80

Asp Trp Pro Asp Ser Pro Pro Glu Pro Ala Pro Glu Ala Arg Pro
                85                  90                  95

Thr Ala Ala Ala Pro Arg Pro Arg Ser Pro Pro Gly Ala Gly Pro
            100                 105                 110

Gly Gly Gly Ala Asn Pro Ser His Pro Pro Ser Arg Pro Phe Arg Leu
        115                 120                 125

Pro Pro Arg Leu Ala Leu Arg Leu Arg Val Thr Ala Glu His Leu Ala
    130                 135                 140

Arg Leu Arg Leu Arg Arg Ala Gly Gly Glu Gly Ala Pro Glu Pro Pro
145                 150                 155                 160

Ala Thr Pro Ala Thr Pro Ala Thr Pro Ala Thr Pro Ala Thr Pro Ala
                165                 170                 175

Thr Pro Ala Thr Pro Ala Thr Pro Ala Thr Pro Ala Thr Pro Ala Arg
            180                 185                 190

Val Arg Phe Ser Pro His Val Arg Val Arg His Leu Val Val Trp Ala
        195                 200                 205

Ser Ala Ala Arg Leu Ala Arg Arg Gly Ser Trp Ala Arg Glu Arg Ala
    210                 215                 220

Asp Arg Ala Arg Phe Arg Arg Val Ala Glu Ala Glu Ala Val Ile
225                 230                 235                 240

Gly Pro Cys Leu Gly Pro Glu Ala Arg Ala Arg Ala Leu Ala Arg Gly
                245                 250                 255

Ala Gly Pro Ala Asn Ser Val
            260
```

```
<210> SEQ ID NO 4
<211> LENGTH: 1399
<212> TYPE: DNA
<213> ORGANISM: Herpes simplex virus 1

<400> SEQUENCE: 4
tttaaagtcg cggcggcgca gcccgggccc ccgcggccg agacgagcga gttagacagg      60
caagcactac tcgcctctgc acgcacatgc ttgcctgtca aactctacca ccccggcacg    120
ctctctgtct ccatggcccg ccgcgccgc catcgcggcc cccgccgccc ccggccgccc     180
gggcccacgg gcgccgtccc aaccgcacag tcccaggtaa cctccacgcc caactcggaa   240
cccgcggtca ggagcgcgcc ccgcggccgcc ccgccgccgc ccccgccag tgggcccccg   300 ccttcttgtt cgctgctgct gcgccagtgg ctccacgttc ccgagtccgc gtccgacgac   360
gacgatgacg acgactggcc ggacagcccc ccgcccgagc cggcgccaga ggcccggccc   420
accgccgccg ccccccgccc ccggtcccca ccgcccggcg cgggcccggg gggcggggct   480
aacccctccc acccccctc acgccccttc cgccttccgc cgcgcctcgc cctccgcctg    540
cgcgtcaccg cagagcacct ggcgcgcctg cgcctgcgac gcgcgggcgg ggaggggggcg  600 ccggagcccc ccgcgacccc cgcgaccccc gcgaccccg cgaccccgc gaccccgcg     660 accccgcga ccccgcgac cccgcgacc cccgcgacc ccgcgcgggt gcgcttctcg       720
ccccacgtcc gggtgcgcca cctggtggtc tgggcctcgg ccgcccgcct ggcgcgccgc   780
ggctcgtggg cccgcgagcg ggccgaccgg gctcggttcc ggcgccgggt ggcggaggcc   840
gaggcggtca tcgggccgtg cctggggccc gaggcccgtg cccgggccct ggcccgcgga   900
gccggcccgg cgaactcggt ctaacgttac acccgaggcg gcctgggtct tccgcggagc   960
tcccgggagc tccgcaccaa gccgctctcc ggagagacga tggcaggagc cgcgcatata  1020
tacgctggga gccggcccgc ccccgaggcg ggcccgccct cggagggcgg gactggccaa  1080
tcggcggccg ccagcgcggc ggggcccggc caaccagcgt ccgccgagtc ttcggggccc  1140
ggcccactgg gcgggagtta ccgcccagtg ggccgggccg cccacttccc ggtatggtaa  1200
ttaaaaactt acaagaggcc ttgttccgct tcccggtatg gtaattagaa actcattaat  1260
gggcggcccc ggccgcccct cccgcttccg gcaattcccg cggcccttaa tgggcaaccc  1320
cggtattccc cgcctcccgc gccgcgcgta accactccct tggggttccg ggttatgcta  1380
attgcttttt tggcggaat                                                1399

<210> SEQ ID NO 5
<211> LENGTH: 18
<212> TYPE: DNA
<213> ORGANISM: Artificial
<220> FEATURE:
<223> OTHER INFORMATION: Primer

<400> SEQUENCE: 5
atgagtacaa cgagtaag                                                   18

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
ctagtattca gcacctgctt                                                 20
```

```
<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
atgggagaga atgctgatgg                                              20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tcagaatgca gggttcattt                                              20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
atgagtgaga acaataagaa                                              20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
tcattcccca ttccagcttg                                              20

<210> SEQ ID NO 11
<211> LENGTH: 27
<212> TYPE: DNA
<213> ORGANISM: Artificial
<220> FEATURE:
<223> OTHER INFORMATION: Primer

<400> SEQUENCE: 11
atgagtacaa atggtgatga tcatcag                                      27

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
attgcctgct tctatataca ttcttgc                                      27

<210> SEQ ID NO 13
<211> LENGTH: 20
<212> TYPE: DNA
<213> ORGANISM: Artificial
<220> FEATURE:
<223> OTHER INFORMATION: Primer
```

```
<400> SEQUENCE: 13
cgcagctagg aataatggaa                                              20

<210> SEQ ID NO 14
<211> LENGTH: 19
<212> TYPE: DNA
<213> ORGANISM: Artificial
<220> FEATURE:
<223> OTHER INFORMATION: Primer

<400> SEQUENCE: 14
ttatgaccgc acttactgg                                               19

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
cgcagctagg aataatggaa                                              20

<210> SEQ ID NO 16
<211> LENGTH: 20
<212> TYPE: DNA
<213> ORGANISM: Artificial
<220> FEATURE:
<223> OTHER INFORMATION: Primer'

<400> SEQUENCE: 16
ttatgacccg cacttactgg                                              20

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
ctggaatcgg acagcagccg g                                            21

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
gaggcgcgac cacacactgt                                              20

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19
actaacttcg actggcccett c                                           21

<210> SEQ ID NO 20
```

```
<211> LENGTH: 21
<212> TYPE: DNA
<213> ORGANISM: Artificial
<220> FEATURE:
<223> OTHER INFORMATION: Primer

<400> SEQUENCE: 20
ccgtacatgt cgatgttcaa c                                              21

<210> SEQ ID NO 21
<211> LENGTH: 17
<212> TYPE: DNA
<213> ORGANISM: Artificial
<220> FEATURE:
<223> OTHER INFORMATION: Primer

<400> SEQUENCE: 21
gccgccgcct actaccc                                                   17

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
gctgccgcga tcgtgatg                                                  18
```

COMPOSITIONS AND METHODS USING HERPES SIMPLEX VIRUS

FEDERALLY SPONSORED RESEARCH

This invention was made with government support under the National Institutes of Health grant number NIH AI 046665. The government has certain rights in the invention.

CROSS REFERENCE TO RELATED APPLICATIONS

This application claims priority to U.S. Provisional Application Nos. 61/225,710, filed on Jul. 15, 2009, and 61/225,736, also filed on Jul. 15, 2009, which are both incorporated by reference in their entirety.

FIELD OF THE INVENTION

The present invention relates to the development and use of $\gamma_1 34.5$ nucleic acid and protein from HSV-1 and/or TANK-binding kinase-1 (TBK1) for identifying compounds for use in preventing or treating HSV-related conditions and diseases.

REFERENCE TO THE SEQUENCE LISTING

Applicant hereby makes reference to the sequence listing, which is contained in a file named "SequenceListing.txt" (18 Kb, created Feb. 15, 2013) and incorporated herein by reference.

BACKGROUND

HSV-1 infections are common and affect between 70 and 80 percent of the total population in the United States. Several manifestations of HSV disease cause significant morbidity and mortality. For example, HSV disease in an immunocompromised host will often result in progressive infection, particularly in stem cell transplant recipients. HSV infection is also a risk factor in HIV infection and transmission. HSV-1 is a human pathogen responsible for localized mucocutaneous lesions and encephalitis, and is transmitted via body secretions and/or direct oral and sexual contact.

During infection of a cell, expression of HSV proteins interferes with the induction of antiviral immunity. One such protein, the $\gamma_1 34.5$ protein, consists of 263 amino acids and is essential in the pathogenesis of HSV infection. In the targeted/infected host cell, TBK1 is a key component of Toll-like receptor-dependent and -independent signaling pathways. In response to microbial components, TBK1 activates interferon regulatory factor 3 (IRF3) and cytokine expression.

While the $\gamma_1 34.5$ protein of HSV-1 has been extensively studied and sequenced in various HSV strains, there is scant evidence to show how the $\gamma_1 34.5$ protein is a critical determinant of viral replication. Accordingly, effective use of the $\gamma_1 34.5$ protein for treating HSV-related conditions and diseases has been slight. A method to identify compounds that can prevent or treat HSV-1 and HSV-2-related conditions and diseases is desired. Further, a $\gamma_1 34.5$ protein-based vaccine having enhanced immunogenicity over other HSV-1 related vaccines is also desired.

SUMMARY OF THE INVENTION

Provided herein is a method for screening for a modulator of $\gamma_1 34.5$. The method may comprise providing a cell, which contains TBK1, contacting the cell with a $\gamma_1 34.5$ nucleic acid or HSV, and a candidate modulator compound, and measuring a HSV infection biological parameter. The HSV may be HSV-1 or HSV-2. The $\gamma_1 34.5$ nucleic acid may be contained within a vector, which is contacted with the cell. The HSV may contain a nucleic acid encoding $\gamma_1 34.5$. A modulator of $\gamma_1 34.5$ is identified by a change in one or more HSV-1 infection biological parameters as compared to a control. Such parameters include virus yield, interferon regulatory factor-3 (IRF3) phosphorylation, interferon regulatory factor-7 (IRF7) phosphorylation, nuclear translocation of IRF3, TBK1 phosphorylation, interferon expression, and interferon stimulated gene expression. The cell may be a mammalian cell, such as a mammalian dendritic cell, a Vero cell, a 293T cell, a HEL cell, a CHO cell, or a HeLa cell. The cell may express TBK1 and/or IRF3 from one or more transfected nucleic acids and/or from endogenous nucleic acid. The HSV may be contacted with the cell before or after the candidate modulator compound is contacted with the cell.

Also provided herein is a method for screening for a modulator of TBK1. Similarly to the above-described method for screening for modulators of $\gamma_1 34.5$, a cell is provided that comprises TBK1. However, the cell is then contacted with a $\gamma_1 34.5$ null or $\gamma_1 34.5$ truncation HSV mutant and a candidate modulator compound. A modulator is again identified by a change in one or more HSV infection biological parameters as compared to a control. Such parameters include virus yield, interferon regulatory factor-3 (IRF3) phosphorylation, nuclear translocation of IRF3, TBK1 phosphorylation, interferon expression, and interferon stimulated gene expression. The cell may be a mammalian cell, such as a mammalian dendritic cell, a Vero cell, a 293T cell, a HEL cell, a CHO cell, or a HeLa cell. The cell may express TBK1 and/or IRF3 from one or more transfected nucleic acids and/or from endogenous nucleic acid. The HSV-1 may be contacted with the cell before or after the candidate modulator compound is contacted with the cell.

Also provided herein is an attenuated HSV-1 virus that comprises a deletion, which removes a fragment of the amino-terminal domain of $\gamma_1 34.5$. This deletion is present in at least one copy of the polynucleotides or genes encoding $\gamma_1 34.5$. The removed fragment may consist of amino acid 1 to amino acid 30 or amino acid 30 to amino acid 72 of SEQ ID NO:3. The removed fragment may not be from the amino-terminal domain of $\gamma_1 34.5$. Such a fragment may consist of amino acid 159 to amino acid 263 of SEQ ID NO:3.

The attenuated HSV-1 virus may be combined with an adjuvant to form an immunogenic composition. This composition may be used to provoke an immune response against HSV strains in a subject and/or to prevent or reduce the incidence of or severity of a clinical sign associated with HSV infection. Examples of clinical signs include keratitis, gingivostomatitis, pharyngitis, encephalitis, and mucocutaneous lesions.

BRIEF DESCRIPTION OF THE DRAWINGS

FIG. 1 shows the inhibition of ISG54 and ISG56 induction in infected mouse embryonic fibroblasts by HSV-1 $\gamma_1 34.5$ protein.

FIG. 12 shows activation of naïve CD4 T cells by dendritic cells.

DETAILED DESCRIPTION

Figure 2:
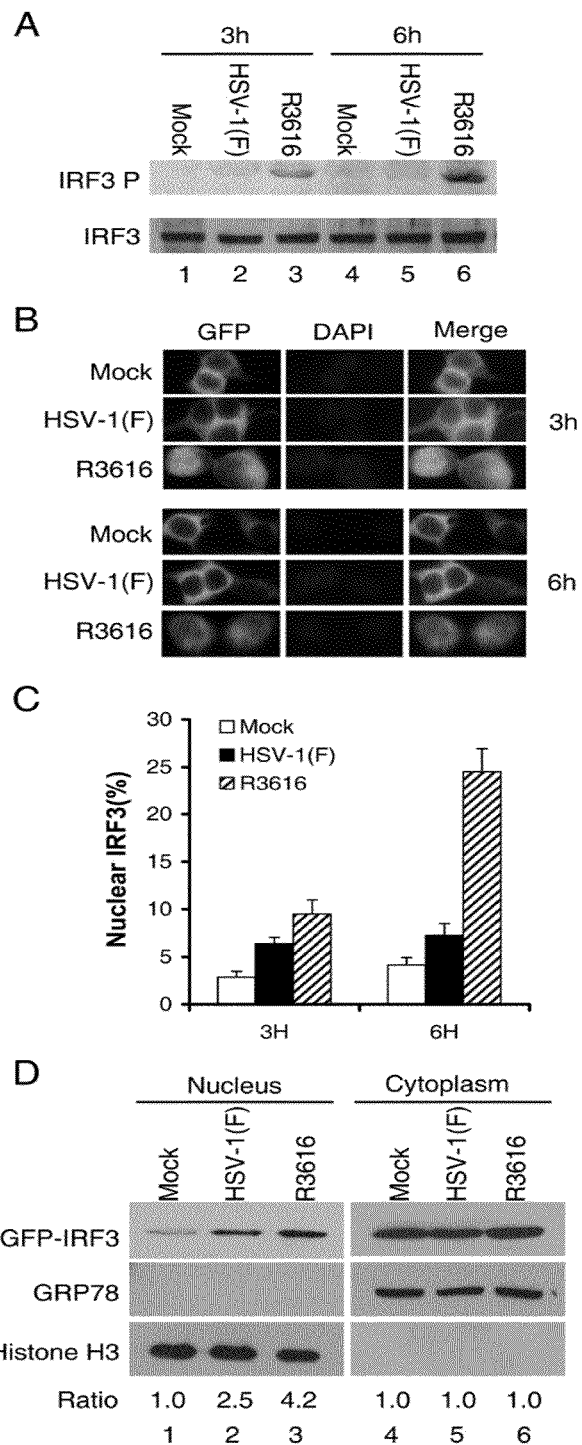
FIG. 2 shows the inhibition of phosphorylation of endogenous IRF3 in infected cells by $\gamma_1 34.5$ protein.

The inventor has discovered that TBK1 is a cellular target of the $\gamma_1 34.5$ protein and that $\gamma_1 34.5$ protein-TBK1 interaction is necessary for HSV infection and replication. The inventor has used this discovery to develop methods of screening for compounds that modulate the activity of the $\gamma_1 34.5$ protein; to develop methods of screening for compounds that modulate the activity of TBK1; and to identify mutant forms of the $\gamma_1 34.5$ protein, which can be used as vaccine platforms. Compounds that modulate either of $\gamma_1 34.5$ protein or TBK1 may be used in methods to treat HSV-related conditions and diseases including cancer.

1. DEFINITIONS

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Fragment

"Fragment" as used herein may mean a portion or a nucleic acid that encodes a polypeptide. The fragments may be DNA fragments selected from at least one of the various encoding nucleotide sequences of the present invention, including SEQ ID NOS: 2 and 4. The DNA fragments may be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length DNA fragments may be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" may also mean a polypeptide fragment. The fragment may be polypeptide fragment selected from at least one of the various encoding polypeptide sequences of the present invention, including SEQ ID NOS: 1 and 3. The polypeptide fragments may be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length Polypeptide fragments may be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

b. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

c. Immune Response

"Immune response" as used herein may mean the activation of a host's immune system, e.g., that of a mammal, in response to the introduction of a $\gamma_1 34.5$ protein, or variant thereof, or exogenous gene thereof, via the provided HSV-related vaccines. The immune response can be in the form of a cellular or humoral response, or both.

d. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

e. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

f. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

g. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. METHODS OF SCREENING

Provided herein is a method for screening for compounds that modulate the $\gamma_1 34.5$. The method comprises providing a cell that comprises TBK1, contacting the cell with a $\gamma_1 34.5$ nucleic acid or HSV-1, which contains a polynucleotide that expresses $\gamma_1 34.5$, and a candidate modulator compound, and measuring an infection biological parameter.

Also provided herein is a method for screening for modulators of TBK1. The method comprises providing a cell that comprises TBK1, contacting the cell with a variant of HSV-1, which is null for $\gamma_1 34.5$, and a candidate modulator compound, and measuring a HSV-1 infection biological parameter. A modulator of the $\gamma_1 34.5$ protein or TBK1 may be identified by a change in the HSV-1 infection parameter as compared to a control. The herein described screening methods may be performed in a variety of formats, including in vitro, cell-based, and in vivo assays.

a. TBK1

TBK1 is a kinase that plays a necessary role in cellular antiviral mechanisms that operate in a cell-type and time-dependent manner. TBK1 is an essential kinase that phosphorylates interferon regulatory factor 3 (IRF3) as well as the closely related interferon regulatory factor 7 (IRF7), each of which translocates to the nucleus and induces antiviral genes, such as interferon-$\alpha/\beta$ and interferon-stimulated gene 56 (ISG56).

TBK1 and IRF3 belong to a signaling pathway that mediates induction of gene expression, including a mixture of secreted factors, which, in concert, mediate proliferative activity toward endothelial cells. TBK1 governs this pathway and is expressed at significant levels in many solid tumors. This pattern of expression and the decreased expression of angiogenic factors in cultured cells upon RNA-interference-mediated ablation has previously identified TBK1 as an important protein for vascularization and subsequent tumor growth and a target for cancer therapy. See, for example, Korherr et al., PNAS (Mar. 14, 2006) Vol. 103(11) pp. 4240-4245. Accordingly, the identification of modulators of TBK1 may be useful in methods for treating cancer.

The method for screening candidate modulator compounds of TBK1 or $\gamma_1 34.5$ employs the use of TBK1, or a variant thereof. TBK1 may have the amino acid sequence provided in SEQ ID NO:1. TBK1 may be encoded by SEQ ID NO:2. A variant of TBK1 may be 95%, 96%, 97%, 98%, or 99% identical to SEQ ID NO:1. A variant of TBK1 may be between 80% and 95% identical to SEQ ID NO:1. TBK1 may be expressed from an endogenous or exogenous nucleic acid. A cell may be transfected with an exogenous nucleic acid encoding TBK1. The exogenous nucleic acid may be a vector comprising SEQ ID NO:2, or a variant thereof. An endogenously expressed TBK1 may be expressed from the cell genome.

TABLE 1

| SEQ ID NO: 1<br>TBK1 Amino Acid Sequence | MQSTSNHLWLLSDILGQGATANVFRGRHKK<br>TGDLFAIKVFNNIS |
|---|---|
| | FLRPVDVQMREFEVLKKLNHKNIVKLFAIEE<br>ETTTRHKVLIMEFCPCGSLYTVLEEPS |
| | NAYGLPESEFLIVLRDVVGGMNHLRENGIVH<br>RDIKPGNIMRVIGEDGQSVYKLTDFGA |
| | ARELEDDEQFVSLYGTEEYLHPDMYERAVL<br>RKDHQKKYGATVDLWSIGVTFYHAATGS |
| | LPFRPFEGPRRNKEVMYKIITGKPSGAISGVQ<br>KAENGPIDWSGDMPVSCSLSRGLQVL |
| | LTPVLANILEADQEKCWGFDQFFAETSDILH<br>RMVIHVFSLQQMTAHKIYIHSYNTATI |
| | FHELVYKQTKIISSNQELIYEGRRLVLEPGRL<br>AQHFPKTTEENPIFVVSREPLNTIGL |
| | IYEKISLPKVHPRYDLDGDASMAKAITGVVC<br>YACRIASTLLLYQELMRKGIRWLIELI |
| | KDDYNETVHKKTEVVITLDFCIRNIEKTVKV<br>YEKLMKINLEAAELGEISDIHTKLLRL |
| | SSSQGTIETSLQDIDSRLSPGGSLADAWAHQE<br>GTHPKDRNVEKLQVLLNCMTEIYYQF |
| | KKDKAERRLAYNEEQIHKFDKQKLYYHATK<br>AMTHFTDECVKKYEAFLNKSEEWIRKML |
| | HLRKQLLSLTNQCFDIEEEVSKYQEYTNELQ<br>ETLPQKMFTASSGIKHTMTPIYPSSNT |

TABLE 1-continued

LVEMTLGMKKLKEEMEGVVKELAENNHILE
RFGSLTMDGGLRNVDCL

SEQ ID NO: 2
TBK1 Nucleic Acid Sequence

```
gccggcggtg gcgcggcgga gacccggctg gtataacaag
aggattgcct gatccagcca agatgcagag cacttctaat
catctgtggc ttttatctga tattttaggc caaggagcta
ctgcaaatgt cttcgtgga agacataaga aaactggtga
tttatttgct atcaaagtat ttaataacat aagcttcctt
cgtccagtgg atgttcaaat gagagaattt gaagtgttga
aaaaactcaa tcacaaaaat attgtcaaat tatttgctat
tgaagaggag acaacaacaa gacataaagt acttattatg
gaattttgtc catgtgggag tttatacact gttttagaag
aaccttctaa tgcctatgga ctaccagaat ctgaattctt
aattgttttg cgagatgtgg tgggtggaat gaatcatcta
cgagagaatg gtatagtgca ccgtgatatc aagccaggaa
atatcatgcg tgttataggg gaagatggac agtctgtgta
caaactcaca gattttggtg cagctagaga attagaagat
gatgagcagt ttgtttctct gtatggcaca gaagaatatt
tgcaccctga tatgtatgag agagcagtgc taagaaaaga
tcatcagaag aaatatggag caacagttga tctttggagc
attggggtaa cattttacca tgcagctact ggatcactgc
catttagacc ctttgaaggg cctcgtagga ataaagaagt
gatgtataaa ataattacag gaaagccttc tggtgcaata
tctggagtac agaaagcaga aaatggacca attgactgga
gtggagacat gcctgtttct tgcagtcttt ctcggggtct
tcaggttcta cttaccctg ttcttgcaaa catccttgaa
gcagatcagg aaaagtgttg gggttttgac cagttttttg
cagaaactag tgatatactt caccgaatgg taattcatgt
tttttcgcta caacaaatga cagctcataa gatttatatt
catagctata atactgctac tatatttcat gaactggtat
ataaacaaac caaaattatt tcttcaaatc aagaacttat
ctacgaaggg cgacgcttag tcttagaacc tggaaggctg
gcacaacatt tccctaaaac tactgaggaa aaccctatat
ttgtagtaag ccgggaacct ctgaatacca taggattaat
atatgaaaaa atttccctcc ctaaagtaca tccacgttat
gatttagacg gggatgctag catggctaag gcaataacag
gggttgtgtg ttatgcctgc agaattgcca gtaccttact
gctttatcag gaattaatgc gaaaggggat acgatggctg
attgaattaa ttaaagatga ttacaatgaa actgttcaca
aaaagacaga agttgtgatc acattggatt tctgtatcag
aaacattgaa aaaactgtga aagtatatga aaagttgatg
aagatcaacc tggaagcggc agagttaggt gaaatttcag
acatacacac caaattgttg agactttcca gttctcaggg
aacaatgaaa accagtcttc aggatatcga cagcagatta
tctccaggtg gatcactggc agacgcatgg gcacatcaag
aaggcactca tccgaaagac agaaatgtag aaaaactaca
agtcctgtta aattgcatga cagagattta ctatcagttc
aaaaagaca aagcagaacg tagattagct tataatgaag
aacaaatcca caaatttgat aagcaaaaac tgtattacca
tgccacaaaa gctatgacgc actttacaga tgaatgtgtt
aaaaagtatg aggcattttt gaataagtca gaagaatgga
taagaaagat gcttcatctt aggaaacagt tattatcgct
gactaatcag tgtttgata ttgaagaaga agtatcaaaa
tatcaagaat atactaatga gttacaagaa actctgcctc
agaaaatgtt tacagcttcc agtggaatca acataccat
gaccccaatt tatccaagtt ctaacacatt agtagaaatg
actcttggta tgaagaaatt aaaggaagag atggaagggg
tggttaaaga acttgctgaa aataaccaca tttagaaag
gtttggctct ttaaccatgg atggtggcct tcgcaacgtt
gactgtcttt agctttctaa tagaagttta agaaaagttt
ccgtttgcac aagaaaataa cgcttgggca ttaaatgaat
gccttatag atagtcactt gtttctacaa ttcagtattt
gatgtggtcg tgtaaatatg tacaatattg taaatacata
aaaaatatac aaatttttgg ctgctgtgaa gatgtaattt
tatctttaa catttataat tatatgagga aatttgacct
cagtgatcac gagaagaaag ccatgaccga ccaatatgtt
gacatactga tcctctactc tgagtgggc taaataagtt
attttctctg accgcctact ggaaatattt ttaagtggaa
ccaaaatagg catccttaca aatcaggaag actgacttga
cacgtttgta aatggtagaa cggtggctac tgtgagtggg
gagcagaacc gcaccactgt tatactggga taacaatttt
tttgagaagg ataaagtggc attatttat tttacaaggt
gcccagatcc cagtatcct tgtatccatg taatttcaga
tgaattatta agcaaacatt ttaaagtgaa ttcattatta
aaaactattc attttttttcc tttggccata aatgtgtaat
tgtcattaaa attctaaggt catttcaact gttttaagct
gtatatttct ttaattctgc ttactatttc atggaaaaaa
ataaatttct caattttaat gt
``` b. γ₁34.5 and HSV

The herein described methods for screening candidate modulator compounds of the γ₁34.5 protein or TBK1 may employ the use of the γ₁34.5 protein, a variant thereof, and/or a vector comprising a nucleic acid encoding the γ₁34.5 protein (SEQ ID NO:4) or TBK1 (SEQ ID NO:2), or variants thereof. A variant of γ₁34.5 may be 95%, 96%, 97%, 98%, or 99% identical to SEQ ID NO:3 or SEQ ID NO:4. A variant of γ₁34.5 may be between 80% and 95% identical to SEQ ID NO:3 or SEQ ID NO:4. A variant γ₁34.5 may be truncated. A variant γ₁34.5 may have a fragment removed from the amino-terminal domain. The removed fragment may correspond to amino acid 1 to amino acid 30 of SEQ ID NO:3, amino acid 1 to amino acid 146 of SEQ ID NO:3, amino acid 30 to amino acid 72 of SEQ ID NO:3, or amino acid 159 to 263 of SEQ ID NO:3. The HSV may be null for γ₁34.5.

The nucleic acid encoding the γ₁34.5 protein may be endogenous to HSV. See SEQ ID NO:4.

The HSV may be HSV-1 or HSV-2. Upon infecting a cell, HSV may or may not express γ₁34.5 protein or a variant thereof. Upon HSV infection, if γ₁34.5 is expressed, γ₁34.5 interacts with TBK1. This interaction blocks IRF3 activation and also blocks the subsequent induction of antiviral genes early in HSV infection. γ₁34.5 protein may prevent translational arrest mediated by double-stranded (ds) RNA-activated protein kinase PKR (eIF2aK2) in a cell.

TABLE 2

| | |
|---|---|
| SEQ ID NO: 3<br>γ₁34.5 Amino Acid Sequence | MARRRRHRGPRRPRPPGPTGAVPTAQSQVTS<br>TPNSEPAVRSAPA<br><br>AAPPPPPASGPPPSCSLLLRQWLHVPESASDD<br>DDDDDWPDSPPPEPAPEARPTAAAPR<br><br>PRSPPPGAGPGGGANPSHPPSRPFRLPPRLAL<br>RLRVTAEHLARLRLRRAGGEGAPEPP<br><br>ATPATPATPATPATPATPATPATPATPATPAR<br>VRFSPHVRVRHLVVWASAARLARRGS<br><br>WARERADRARFRRRVAEAEAVIGPCLGPEA<br>RARALARGAGPANSV |
| SEQ ID NO: 4<br>γ₁34.5 Nucleic Acid Sequence | tttaaagtcg cggcggcgca gcccgggccc cccgcggccg<br>agacgagcga gttagacagg caagcactac tcgcctctgc<br>acgcacatgc ttgcctgtca aactctacca ccccggcacg<br>ctctctgtct ccatggcccg ccgccgccgc catcgcggcc<br>cccgccgccc ccggccgccc gggcccacgg gcgccgtccc<br>aaccgcacag tcccaggtaa cctccacgcc caactcggaa<br>cccgcggtca ggagcgcgcc cgcggccgcc ccgccgccgc<br>cccccgccag tgggcccccg ccttcttgtt cgctgctgct<br>gcgccagtgg ctccacgttc ccagtccgc gtccgacgac<br>gacgatgacg acgactggcc ggacagcccc ccgcccgagc<br>cggcgccaga ggcccggccc accgccgccg ccccccgccc<br>ccggtcccca ccgcccggcg cgggccgggg gggcggggct<br>aaccccctccc accccccctc acgcccttc cgccttccgc<br>cgcgcctcgc cctccgcctg cgcgtcaccg cagagcacct<br>ggcgcgcctg cgcctgcgac gcgcgggcgg ggaggggcg<br>ccggagcccc ccgcgacccc cgcgaccccc gcgaccccg<br>cgacccccgc gacccccgcg accccgcga ccccgcgac<br>ccccgcgacc cccgcgaccc ccgcgcgggt gcgcttctcg<br>ccccacgtcc gggtgcgcca cctggtggtc tgggcctcgg<br>ccgcccgcct ggcgcgccgc ggctcgtggg cccgcgagcg<br>ggccgaccgg gctcggttcc ggcgccgggt ggcggaggcc<br>gaggcggtca tcgggcgtg cctggggccc gaggcccgtg<br>cccgggccct ggcccgcgga gccggcccgg cgaactcggt<br>ctaacgttac acccgaggcg gcctgggtct tccgcggagc<br>tcccgggagc tccgcaccaa gccgctctcc ggagagacga<br>tggcaggagc cgcgcatata tacgctggga gccggcccgc<br>ccccgaggcg ggcccgccct cggagggcgg gactggccaa<br>tcggcggccg ccagcgcggc ggggcccggc caaccagcgt<br>ccgccgagtc ttcggggccc ggcccactgg gcgggagtta<br>ccgcccagtg ggccgggccg cccacttccc ggtatggtaa<br>ttaaaaactt acaagaggcc ttgttccgct tcccggtatg<br>gtaattagaa actcattaat gggcggcccc ggccgccctt<br>cccgcttccg gcaattcccg cggcccttaa tgggcaaccc<br>cggtattccc cgcctcccgc gccgcgcgta accactccct<br>tggggttccg ggttatgcta attgcttttt tggcggaat | c. Cell

Provided herein is a cell that comprises a TBK1. The cell may be any eukaryotic cell. The eukaryotic cell may be any mammalian cell, such as a mammalian dendritic cell, a HeLa cell, a CHO cell, a yeast cell, a human embryonic kidney cell, a HEL cell, or a 293T cell.

The cell may comprise a vector. The vector may express any member of a peptide or cDNA library, or any other peptide or nucleic acid, may be introduced into the cell by any convenient method, which will vary depending on the vector-host system employed. Generally, a vector may be introduced into a host cell by transformation or infection (also known as "transfection") with a virus (e.g., phage) bearing the vector. Yeast cells may be transformed using polyethylene glycol, for example, as taught by Hinnen (1978) *Proc. Natl. Acad. Sci, USA,* 75:1929-33. Mammalian cells are conveniently transformed using the calcium phosphate precipitation method described by Graham, et al. (1978) *Virology*, 52:546 and by Gorman, et al. (1990) *DNA and Prot. Eng. Tech.*, 2:3-10. However, other known methods for introducing DNA into host cells, such as nuclear injection, electroporation, protoplast fusion, and other means also are acceptable for use in the invention.

Cell culture conditions may allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolarity of the culture; and cell density. The adjustment of these factors to promote expression in a particular vector-host cell system is within the level of skill in the art. Principles and practical techniques for maximizing the productivity of in vitro mammalian cell cultures, for example, may be found in Mammalian Cell Biotechnology: a Practical Approach (Butler ed., IRL Press (1991).

Any of a number of well-known techniques for large- or small-scale production of proteins may be employed in expressing the candidate modulator. These may include the use of a shaken flask, a fluidized bed bioreactor, a roller bottle culture system, and a stirred tank bioreactor system. Cell culture may be carried out in a batch, fed-batch, or continuous mode.

(1) Cell Contact

The cell may be contacted with a nucleic acid encoding $\gamma_1 34.5$ protein, or a variant thereof, an HSV virus containing a nucleic acid encoding $\gamma_1 34.5$ protein, or a variant thereof, a nucleic acid encoding TBK1, or a variant thereof, a candidate modulator compound, and/or a nucleic acid encoding a candidate modulator compound.

The time of contact may vary depending upon the nucleic acid or compound and any accompanying reagents employed in the method and can readily be determined by the person using the method.

d. Candidate Modulator

A candidate modulator compound may be any compound wherein the characterization of the compound's ability to modulate is desirable. Exemplary candidate compounds or substrates include small molecules, peptides, nucleic acids, antibodies, polypeptides, drugs, and organic compounds.

The candidate modulator may be present within a library (i.e., a collection of compounds). Such candidates may, for example, be encoded by DNA molecules within an expression library. Test substances may be present in conditioned media or in cell extracts. Other such test substances include compounds known in the art as "small molecules," which have molecular weights less than $10^5$ daltons, preferably less than $10^4$ daltons and still more preferably less than $10^3$ daltons. Such test substances may be provided as members of a combinatorial library, which includes synthetic agents (e.g., peptides) prepared according to multiple predetermined chemical reactions. Those having ordinary skill in the art will appreciate that a diverse assortment of such libraries may be prepared according to established procedures, and members of a library of substances can be simultaneously or sequentially screened as described herein.

The screening methods may be performed in a variety of formats, including in vitro, cell-based and in vivo assays. Any cells may be used with cell-based assays.

Methods for recovery of the candidate compound(s) are well-known and vary depending on the expression system employed. A compound including a signal sequence may be recovered from the culture medium. The compound may also be expressed intracellularly and recovered from cell lysates.

The modulator compound, or candidate modulator compound, may be purified from culture medium or a cell lysate by any method capable of separating the compound from one or more components of the host cell or culture medium. The compound may be separated from host cell and/or culture medium components that would interfere with the intended use of the compound. As a first step, the culture medium or cell lysate may be centrifuged or filtered to remove cellular debris. The supernatant may then typically concentrated or diluted to a desired volume or diafiltered into a suitable buffer to condition the preparation for further purification.

The compound may then be further purified using well-known techniques. The technique chosen will vary depending on the properties of the compound. For example, the compound may be purified using an affinity column containing the cognate binding partner of a binding member of the compound. For instance, the compound fused with green fluorescent protein, hemagglutinin, or FLAG epitope tags or with hexahistidine or similar metal affinity tags may be purified by fractionation on an affinity column. Any of TBK1, $\gamma_1 34.5$ protein, or candidate modulator compounds may be fused to one or more such tags.

Modulators of TBK1 or $\gamma_1 34.5$ protein can also be further evaluated, detected, cloned, sequenced, and the like, either in solution or after binding to a solid support. For recovery of an expressed candidate compound, the host cell may be cultured under conditions suitable for cell growth and expression and the expressed compound recovered from a cell lysate or, if the candidate compounds are secreted, from the culture medium. In particular, the culture medium may contain appropriate nutrients and growth factors for the host cell employed. The nutrients and growth factors are, in many cases, well known or may be readily determined empirically by those skilled in the art. Suitable culture conditions for mammalian host cells, for instance, are described in Mammalian Cell Culture (Mather ed., Plenum Press 1984) and in Barnes and Sato (1980) Cell 22:649.

e. Nucleic Acid Vector

Also provided herein is a vector that comprises a nucleic acid that encodes $\gamma_1 34.5$ protein, or a variant thereof, TBK1, or a variant thereof, and/or a candidate modulator compound.

The vector may be a nucleic acid sequence containing an origin of replication. A vector may be a vector, bacteriophage, bacterial artificial chromosome or yeast artificial chromosome. A vector may be a DNA or RNA vector. A vector may be either a self-replicating extrachromosomal vector or a vector which integrates into a host genome.

The vector may be an expression vector, which may include one or more control sequences capable of effecting and/or enhancing the expression of the proteins, or variants thereof, as discussed herein. Control sequences for expression in eukaryotic cells may include a promoter, an enhancer, and a transcription termination sequence, for example a polyadenylation signal).

The vector may also include other sequences, such as, for example, nucleic acid sequences encoding a signal sequence or an amplifiable gene. A signal sequence may direct the secretion of a polypeptide fused thereto from a cell expressing the protein. In the expression vector, nucleic acid encoding a signal sequence may be linked to a polypeptide coding sequence so as to preserve the reading frame of the polypeptide coding sequence.

f. Infection Parameters

Candidate modulator compounds of $\gamma_1 34.5$ protein or TBK1 may be determined to be modulators based upon measuring any one or more of HSV virus infection parameters and comparing to a control. These parameters may be biochemical. These parameters may include interferon expression, interferon stimulated gene (ISG) expression, virus yield, TBK1 phosphorylation, phosphorylation or targeting of one or more proteins downstream of TBK1, such as IRF-3 or IRF-7, and/or nuclear translocation of IRF3. Virus yield may be measured in plaque forming units (pfu). As compared to a control cell, the virus yield of a cell comprising TBK1, and contacted with HSV and a candidate modulator compound, may be higher or lower than the control cell. For example, when the modulator and a $\gamma_1 34.5$ null HSV virus are brought into contact with a cell comprising TBK1, the modulator of TBK1 may result in an increase in virus yield, as compared to a control.

g. Control Cells

The method of screening and identifying modulators of $\gamma_1 34.5$ protein or TBK1 may use control cells in the analysis. Control calls may be contacted by the candidate modulator compound and compared with cells comprising TBK1 and contacted with an HSV. The control cells can be used to aid in the identification of $\gamma_1 34.5$ protein or TBK1 modulating compounds from a pool or library of candidates. For example, a positive control cell for identifying a candidate modulator that inhibits $\gamma_1 34.5$ protein may be an HSV virus-infected cell that does not express or comprise TBK1. A negative control in a screen for modulators of TBK1 may comprise contacting the candidate modulator compound with a cell that does not express TBK1. Other controls may include the use of known TBK1 or $\gamma_1 34.5$ protein inhibitors.

3. VACCINE PLATFORM a. HSV Vaccine

Provided herein is an attenuated HSV virus for use as an immunogenic composition for the prevention or amelioration of HSV infection. The HSV virus may be characterized by having a fragment deleted from one or both N-termini of the $\gamma_1 34.5$ nucleotide sequences. The fragment that is deleted from one or both N-termini of the $\gamma_1 34.5$ nucleotide sequences may contain amino acid 1 to amino acid 10 of SEQ ID NO:3, amino acid 1 to amino acid 15 of SEQ ID NO:3, amino acid 1 to amino acid 20 of SEQ ID NO:3, amino acid 1 to amino acid 25 of SEQ ID NO:3, amino acid 31 to amino acid 72 of SEQ ID NO:3, amino acid 35 to amino acid 70 of SEQ ID NO:3, amino acid 40 to amino acid 65 of SEQ ID NO:3, amino acid 165 to amino acid 263 of SEQ ID NO:3, amino acid 170 to amino acid 263 of SEQ ID NO:3, amino acid 180 to amino acid 263 of SEQ ID NO:3, amino acid 200 to amino acid 263 of SEQ ID NO:3, and/or amino acid 230 to amino acid 263 of SEQ ID NO:3.

The $\gamma_1 34.5$ fragment that is deleted from one or both N-termini may contain amino acid 1 to amino acid 30 of SEQ ID NO:3; amino acid 1 to amino acid 146 of SEQ ID NO:3; amino acid 30 to amino acid 72 of SEQ ID NO:3; or amino acid 159 to amino acid 263 of SEQ ID NO:3. The deletion detrimentally affects virulence while retaining the immunogenic character of HSV.

Adjuvant substances that stimulate immunogenicity may be mixed with the attenuated virus in order to improve the immune response to the virus. Examples of adjuvants include EMULSIGEN®-D, monophosphoryl lipid A (MPL) and Freund. Immunological adjuvants have generally been divided into two basic types: aluminum salts and oil emulsions. Aluminum phosphate and hydroxide (alum) adjuvants induce elevated levels of antibody against antigens in alum-based vaccines above those obtained with the corresponding aqueous vaccine. Numerous alum-based vaccines, including methods of preparation thereof, were developed as, for example, disclosed in U.S. Pat. Nos. 5,747,653, 6,013,264, 6,306,404 and 6,372,223. EMULSIGEN®-D is a sterile oil-in-water emulsion free of animal origin ingredients, containing uniformly dispersed, micron size oil droplets and dimethyldioctadecylammonium bromide.

Alternatively, an oil based adjuvant may be used. The main components of the oil-based adjuvants are: oil, emulsifier and immunostimulant. Examples of emulsified oil-based adjuvants are Incomplete Freund's Adjuvant (IFA), consisting of an approximately 50:50 water-in-oil emulsion, and complete Freund's adjuvant (CFA), a similar preparation with inclusion of killed mycobacteria. Examples of improved emulsions as vaccine adjuvants, by enhancing the immunogenicity of the antigen, include submicron emulsions as disclosed in U.S. Pat. No. 5,961,970 and solid fat nanoemulsions as disclosed in U.S. Pat. No. 5,716,637, for example.

The vaccine may be administered orally, intravenously, intramuscularly or subcutaneously. The pharmaceutical composition of the invention may also be administered to other mucous membranes. The pharmaceutical composition is then provided in the form of a suppository, nasal spray or sublingual tablet.

The uptake of the attenuated virus may be facilitated by a number of methods. For instance, a non-toxic derivative of the cholera toxin B subunit, or of the structurally related subunit B of the heal-labile enterotoxin of enterotoxic *Escherichia coli* may be added to the composition, as disclosed in U.S. Pat. No. 5,554,378.

These attenuated viruses offer several advantages over other known HSV viruses developed for prophylactic treatment of HSV: (1) the deletions were selectively chosen to avoid over-attenuation of the HSV virus such that the resulting virus would be efficacious for prophylactic treatment of HSV infections and conditions as well as safe; (2) the deletions related to the N-terminus of the coding sequence for the $\gamma_1 34.5$ protein was selected to ensure replication incompetence yet enhance immunogenicity and efficacy of the virus.

The attenuated virus may be used in therapeutic and/or immunogenic compositions for preventing and treating HSV-related conditions and diseases. The pharmaceutical compositions can be used for the prophylactic treatment of an HSV-related disease or condition and comprises an immunizingly effective amount of an attenuated HSV virus in a suitable pharmaceutical vehicle. The composition may be used to generate a neutralizing immune response to HSV infection, for prophylactic treatment of HSV infection, and for prevention of recurrent HSV disease symptoms.

The composition may be used in a method to reduce the incidence of or severity of a clinical sign associated with HSV infection. Such a method may comprise the step of administering the immunogenic composition to a subject in need thereof, wherein the reduction of the incidence of or the severity of a clinical sign is relative to a subject not receiving the immunogenic composition. Examples of clinical signs include gingivostomatitis, pharyngitis, encephalitis, and mucocutaneous lesions.

A mammal can be inoculated intramuscularly or subcutaneously with a composition comprising an immunity-inducing dose of one or more of the herein described viruses. Other modes of inoculation include surface scarification or inoculation of a body cavity. An effective immunization of a human host may be achieved by one to several inoculations of between 10 and 1,000,000 pfu each, as measured in a susceptible human or nonhuman primate cell lines. Each inoculation may have between 1,000 and 1,000,000, or between 10,000 and 1,000,000, or between 100,000 and 1,000,000, or between 500,000 and 1,000,000 pfu.

Notwithstanding the foregoing, pharmaceutical compositions suitable for use in context of the present invention include compositions wherein the active ingredients are contained in an amount effective to achieve the intended purpose. All formulations for administration should be in dosages suitable for the chosen route of administration. More specifically, a "therapeutically effective" dose means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the compositions described herein can be determined by standard pharmaceutical procedures in cell cultures or experimental animals, e.g., by determining the $IC_{50}$ (the concentration which provides 50% inhibition) and the maximal tolerated dose for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The present invention can be utilized as illustrated by the following non-limiting example.

Example 1

Materials and Methods for Examples 2-6

Cells and Viruses—Vero, HEL, and 293T cells were from the American Type Culture Collection. TBK1+/+ and TBK1−/− MEF were gifts from Dr. Wen-Chen Yeh. Cells were propagated in Dulbecco's modified Eagle's medium supplemented with 5% (Vero and 293T) or 10% (MEF and HEL) fetal bovine serum. HSV-1(F) is a prototype HSV-1 strain used in this study. In recombinant virus R3616, a 1 kb fragment from the coding region of the $\gamma_1 34.5$ gene was deleted. These viral strains were gifts from Dr. Bernard Roizman (University of Chicago).

Plasmids—Plasmids pcDNA3, pTK-Luc and dN200 have been described elsewhere. The FLAG-$\gamma_1 34.5$ plasmids, WT, Δ30, Δ72, Δ106, Δ146, and N159, were constructed by inserting PCR amplified fragments into the BamHI and XhoI sites of pcDNA3. To construct GST-IRF3, a DNA fragment encoding amino acids 380 to 427 from IRF3 was ligated into the BamHI and EcoRI sites of pGEX4-T1. pISG56-Luc was a gift from Ganes Sen (The Cleveland Clinical Research Foundation). Plasmids IFNB and FLAG-TBK1 were gifts from R. Lin, J. Hiscott (McGill University), and U. Siebenlist (NIH). Plasmid GFP-IRF3 was a gift from Nancy Reich (State University of New York, Stony Brook). Plasmid HA-$\gamma_1 34.5$ was a gift from Youjia Cao (Nankai University). To construct HA-TBK1, the TBK1 insert was PCR amplified and cloned into the BamHI and XhoI sites of pcDNA3.

Viral Infections—Cells were infected with viruses at 0.05, 5 or 10 pfu per cell. At indicated time points, virus yields were determined on Vero cells. For interferon assays, cells were untreated or treated with mouse alpha interferon (100 U/ml; Sigma) for 20 h. Cells were then infected with viruses. After adsorption for 2 h, the monolayers were overlaid with DMEM medium and incubated at 37° C. At indicated time points post infection, samples were harvested, viruses were released by three cycles of freezing and thawing, and then titrated on Vero cells. For radioisotope labeling, cells were labeled with [35S] methionine (50 μCi/ml; ICN) in DMEM lacking methionine but supplemented with 2% fetal bovine serum 1 h before harvest. At indicated time points, lysates of cell were subjected to electrophoresis and autoradiography.

RT-PCR and Reporter Assays—Cells were mock infected or infected with viruses at 5 pfu per cell in serum free DMEM. At 1 h after infection, cells were grown in DMEM with 1% fetal bovine serum. At the indicated time points, total RNA was harvested from cells using RNeasy kit (Qiagen). RT-PCR analysis was performed with one-step RT-PCR system according to manufacture protocols (Invitrogen). Primers used were as follows: mouse ISG54 (ATGAGTACAAC-GAGTAAG (SEQ ID NO:5) and (CTAGTATTCAGCACCT-GCTT (SEQ ID NO:6)), mouse ISG56 (ATGGGAGAGAAT-GCTGATGG (SEQ ID NO:7)) and (TCAGAATGCAGGGTTCATTT (SEQ ID NO:8)), Human SG54 (ATGAGTGAGAACAATAAGAA (SEQ ID NO:9)) and (TCATTCCCCATTCCAGCTTG (SEQ ID NO:10)), human ISG56 (ATGAGTACAAATGGTGATGATCATCAG (SEQ ID NO:11) and ATTGCCTGCTTCTATATACATTCT-TGC (SEQ ID NO:12)), human or mouse 18SrRNA (CG-CAGCTAG GAA TAA TGG AA (SEQ ID NO:13)) and (TTA TGACCGCACTT ACTGG (SEQ ID NO:14)). Luciferase reporter assays were performed as described previously. Briefly, 293T cells grown on 12-well plate were transfected with a control plasmid or plasmid vector expressing TBK1 and $\gamma_1 34.5$ variants, along with IFN-β or ISG56 reporter plasmid expressing firefly luciferase using Lipofectamine 2000 (Invitrogen). Total levels of transfected DNA were kept constant with empty vector plasmid. As a control for transfection efficiency, a plasmid containing the *Renilla* luciferase gene driven by the HSV-1 TK promoter was included. At 36 h after transfection, cells were harvested and luciferase activities were measured using the Promega's dual luciferase assay system.

Immunoblotting and Immunoprecipitation Analyses—To analyze protein expression, cells were washed, harvested, and solubilized in disruption buffer containing 50 mM Tris-HCl (pH 7.1), 5% 2-mercaptoethanol, 2% sodium dodecyl sulfate (SDS), and 2.75% sucrose. Samples were then sonicated, boiled, subjected to electrophoresis on denaturing 12% polyacrylamide gels, transferred to nitrocellulose membranes, blocked with 5% nonfat milk, and reacted with antibodies against eIF2α, phosphorylated eIF2α (Cell Signaling Tech.), β-actin (Sigma), HSV-1 (Dako Inc.), FLAG (Sigma), HA (Santa Cruz Biotech), IRF3 (Santa Cruz Biotech), phosphorylated IRF3 (ser396) (Cell Signaling Tech.), and $\gamma_1 34.5$. The membranes were rinsed in phosphate-buffered saline and reacted with donkey anti-rabbit immunoglobulin conjugated to horseradish peroxidase. Protein bands were detected by enhanced chemiluminescence (Amersham Pharmacia Biotech Inc.). To examine protein interactions, 293T cells were transfected with indicated amounts of pcDNA3, FLAG-TBK1, HA-$\gamma_1 34.5$, FLAG-dN200, and IRF3. At 40 h after transfection, cells were harvested and lysed in 50 mM Tris-HCl (pH 7.4) buffer containing 1% NP-40; 0.25% Na-deoxycholate; 150 mM NaCl; 1 mM EDTA; 1 mM 4-(2-Aminoethyl)benzenesulfonyl fluoride hydrochloride; 1 µg/ml Aprotinin/leupeptin/pepstatin; 1 mM $Na_3VO_4$; 1 mM NaF. Lysates were incubated overnight at 40 C with anti-FLAG M2 affinity gel (Sigma) or anti-HA antibody (Applied Biological Materials Inc.) plus protein A/G agarose beads (Santa Cruz Biotechnology). Immunocomplexes captured on the affinity gel or protein A/G agarose beads were subjected to electrophoresis and immunoblotting analysis.

Kinase Assays—Recombinant GST-IRF3 fusion protein was purified from bacterial lysates by affinity chromatography. 293T cells were transfected with pcDNA3, FLAG-TBK1, and HA-$\gamma_1$34.5. At 40 h after transfection, cell lysates were prepared in 20 mM Tris-HCl (pH 7.4) containing 137 mM NaCl; 10% glycerol; 1% Triton X-100; 2 mM EDTA; 50 mM sodium glycerophosphate; 20 mM sodium pyrophosphate; 5 µg/ml aprotinin; 5 µg/ml leupeptin; 1 mM $Na_3VO4$ and 5 mM benzamidine. TBK1 was immunoprecipitated with anti-FLAG affinity gel (Sigma). Immunocomplexes were incubated with recombinant GST-IRF3 (380-427) for 20 min at 30° C. in 25 mM Hepes buffer (pH 7.5) containing 10 mM $MgCl2$, 25 mM sodium-β-glycerophosphate, 5 mM benzamidine, 1 mM $Na_3VO_4$, 0.5 mM dithiothreitol, and 100 µM ATP. Samples were subjected to electrophoresis and immunoblotting analysis with rabbit anti-phospho IRF3 (Ser396).

Fluorescence Microscopy—After transfection or infection, cells were washed with phosphate-buffer saline and fixed with ice cold methanol and acetone for 5 min. Following this step, cells were washed with phosphate-buffer saline and stained with 4',6-diamidino-2-phenylindole (DAPI) (1.5 µg/ml) in the VECTASHIELD mounting medium. Samples were visualized under a fluorescent microscope and images were captured with Zeiss AxioCam MRm camera.

Cell Fractionation Assays—Infected or transfected cells were lysed in phosphate-buffer saline containing 0.4% Nonidet P-40 and protease inhibitor cocktails (Sigma) and kept on ice with gentle inversion. After centrifugation for 3 min, and the nuclei were pelleted and supernatant were transferred to a tube. The nuclei were resuspended in phosphate-buffer saline with 0.4% NP-40 and frozen at −80° C. for 30 min. The cytoplasmic and nuclear fractions were then solubilized in disruption buffer. Samples were subjected to electrophoresis and Western blot analysis with antibodies against IRF3 (Santa Cruz Biotech), GRP78 (BD Transduction Laboratories), and histone H3 (Cell Signaling), respectively.

Example 2

34.5 Null Mutant Activates Antiviral Immunity Early in HSV Infection

Although expressed as a leaky late gene, $\gamma_1$34.5 is also detectable early in infection. To explore the biological function of $\gamma_1$34.5, we measured the induction of ISG54 and ISG56 early in HSV infected cells. Mouse embryonic fibroblasts (MEF) were either mock infected or infected with viruses and mRNA levels were determined by RT-PCR. As illustrated in FIG. 1A, the induction of ISG54 as well as ISG56 was seen in cells infected with the $\gamma_1$34.5 null mutant R3616. The mRNA levels of ISG54 and ISG56 increased as virus infection progressed from 3 h to 6 h. This stimulation was not observed in cells mock infected or infected with wild type HSV-1(F) although comparable levels of 18sRNA were noted in all cells. In correlation, wild type virus, but not the $\gamma_1$34.5 null mutant, expressed the $\gamma_1$34.5 protein at 3 and 6 h after infection (FIG. 1C). Similar results were obtained in human lung fibroblasts (HEL) albeit there was a delay in the kinetics of ISG54 and ISG56 induction by R3616 (FIG. 1B).

Since the onset of viral DNA replication triggers the shutoff of protein synthesis mediated by dsRNA dependent protein kinase PKR, we next asked whether the induction of ISG54 and ISG56 by R3616 was linked to this event. As measured by [35S]methionine labeling, at 3 or 6 h after infection, profiles of protein synthesis were similar in HEL cells infected with HSV-1(F) or R3616 (data not shown). Although eIF-2α was constitutively expressed at comparable levels, there was no detectable eIF-2α phosphorylation regardless of $\gamma_1$34.5 expression (FIG. 1C), suggesting that PKR is not activated early in HSV infection. These phenotypes were also seen in MEF cells. Hence, the expression of $\gamma_1$34.5 abrogated the induction of ISG54 and ISG56 by HSV, which was independent of eIF2α phosphorylation and the shutoff of protein synthesis.

Previous work has demonstrated that IRF3 activation stimulates ISG56 expression in HSV infected cells. We further evaluated phosphorylation of endogenous IRF3 in infected cells. As revealed by immonublotting analysis (FIG. 2A), IRF3 was constitutively expressed in HEL cells. Unlike HSV-1(F), R3616 infection resulted in an appearance of the IRF3 phosphoserine-396 isoform at 3 h after infection (lane 3). This response became evident at 6 h after infection (lane 6). To monitor the cellular localization of IRF3, 293T cells expressing a GFP-IRF3 fusion protein were infected with viruses (FIGS. 2B&C). GFP-IRF3 predominantly localized to the cytoplasm in cells mock infected or infected with HSV-1(F). However, as viral infection proceeded, a significant portion of IRF3 was redistributed to the nucleus in cells infected with R3616 at 6 h after infection. These phenotypes were also seen in cell fractionation analysis. As shown in FIG. 2D, GFP-IRF3 was present in the cytoplasmic fraction of mock infected or virus infected cells. However, little GFP-IRF3 was seen in the nuclear fraction of mock infected cells. In virus infected cells, R3616 stimulated more nuclear translocation of GFP-IRF3 than HSV-1(F). As expected, control proteins GRP78 and histone H3 were detected in the cytoplasmic and nuclear fractions, respectively. Together, these results indicate that early expression of $\gamma_1$34.5 is required to suppress phosphorylation and nuclear translocation of IRF3 in HSV infection.

Example 3

Figure 3:
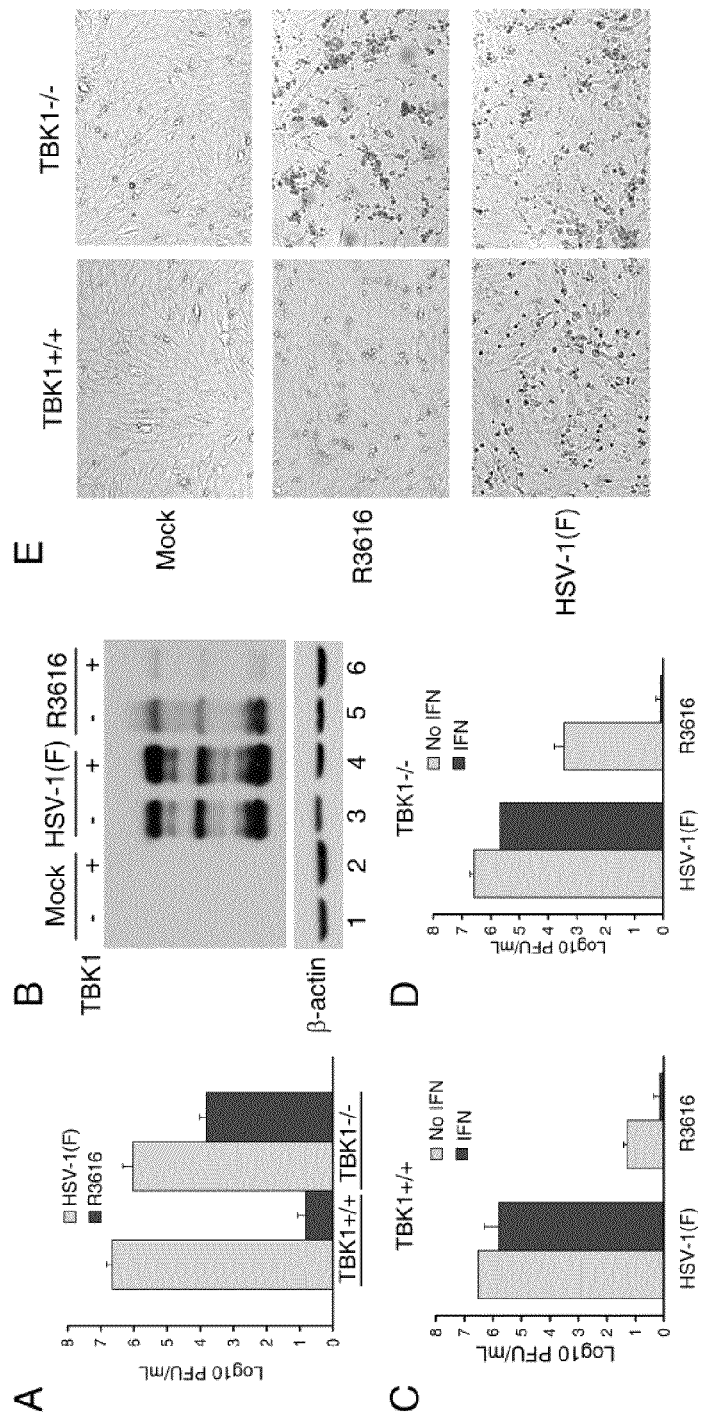
FIG. 3 shows viral replication in TBK1$^{+/+}$ and TBK1$^{-/-}$ cells.

34.5 Null Mutant Replicates More Efficiently in $TBK1^{-/-}$ Cells than in $TBK1^{+/+}$ Cells While HSV induction of antiviral responses involves different components, this process requires TBK1. We hypothesized whether there is a possible link between $\gamma_1$34.5 and the TBK1 pathway. To test this, we investigated viral growth properties in TBK1+/+ and TBK1−/− MEF cells. Specifically, cells were infected with either HSV-1(F) or R3616. At 24 h post infection, virus yields were determined. As shown in FIG. 3A, HSV-1(F) replicated efficiently in both TBK1+/+ and TBK1−/− cells, reaching titers of $4.6 \times 10^6$ and $1 \times 10^6$ pfu/ml, respectively. In striking contrast, R3616 replicated poorly in TBK1+/+ cells, with a virus yield less than 10 pfu/ml. There was approximately $10^5$-fold decrease in viral growth as compared to HSV-1(F). This reduction was attributable to the lack of $\gamma_1$34.5 in R3616. Strikingly, R3616 replicated more efficiently in TBK1−/− cells, with a titer reaching $6.6 \times 10^3$ pfu/ml. There was approximately $10^3$-fold restoration in viral yield. This increase was partial but significant when compared to the replication seen in TBK1+/+ cells. These phenotypes were mirrored by cytopathic effects after viral infection. As illustrated in FIG. 3E, mock-infected cells formed a monolayer, with most cells displaying spindle morphology. HSV-1(F) induced morphological changes in both TBK1+/+ and TBK1−/− cells, where cells formed clumps, indicative of viral replication. In contrast, R3616 induced cytopathic effects only in TBK1−/− cells. Immunoblot analysis revealed that HSV-1(F) produced high levels of viral polypeptides in both TBK1+/+ and TBK1−/− cells, whereas R3616 produced a substantial amount of viral polypeptides only in TBK1−/− cells (FIG. 3B). Collectively, these results show that HSV infection invokes host responses via TBK1 which restricts viral replication in the absence of a $\gamma_1 34.5$ blockade.

To examine whether interferon was able to restore the antiviral activity in the absence of TBK1, we assessed viral responses to IFN-α. As indicated in FIGS. 3C&D, HSV-1(F) replicated well in both TBK1+/+ and TBK1−/− cells, with titers ranging from $3.2 \times 10^6$ to $3.9 \times 10^6$ pfu/ml at 24 h after infection. Treatment with IFN-α had a marginal effect on viral replication. As expected, R3616 replicated more efficiently in untreated TBK1−/− than in TBK1+/+ cells, with a titer of $2.8 \times 10^3$ pfu/ml. When cells were treated with IFN-α R3616 barely replicated, with minimal infectious virus produced. Thus, addition of IFN-α in TBK1−/− cells restored the antiviral activity to R3616. The growth pattern of R3616 resembled that seen in TBK1+/+ cells. Thus, TBK1-induced downstream antiviral molecules likely contribute to the inhibitory effect on viral replication.

Example 4

Figure 4:
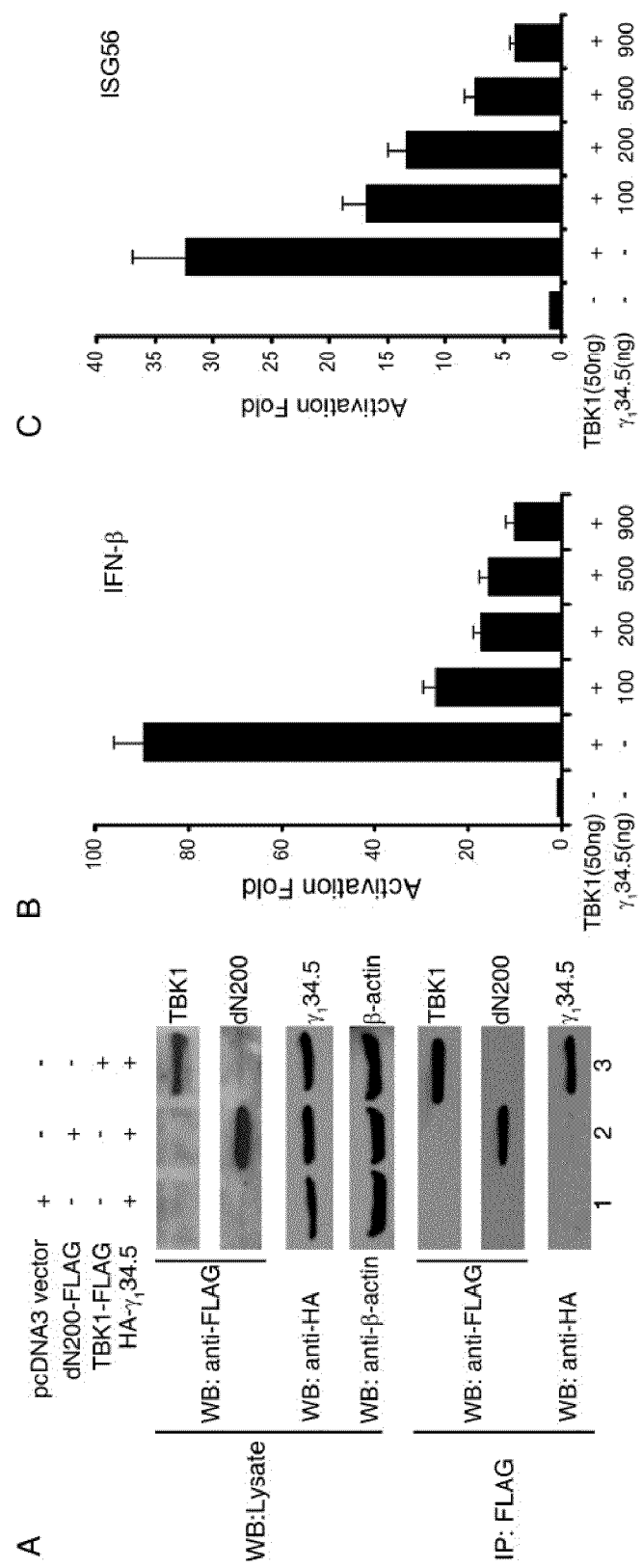
FIG. 4 shows association between $\gamma_1 34.5$ protein and TBK1.

34.5 Protein Associates with TBK1 and Inhibits Activation of IFN-β and ISG56 Promoters The functional link between TBK1 and $\gamma_1 34.5$ raised a possibility that $\gamma_1 34.5$ may interact with TBK1 and suppress its activity. To test this hypothesis, we carried out co-immunoprecipitation experiments in 293T cells transfected with a vector, HA-$\gamma_1 34.5$, FLAG-TBK1, and FLAG-dN200, a truncated form of Ebola VP35. As shown in FIG. 4A, the $\gamma_1 34.5$ protein was co-immunoprecipitated with TBK1, but not with the control protein dN200. Levels of protein expression were comparable in lysates of transfected cells. This data indicates that the $\gamma_1 34.5$ protein specifically associates with TBK1. As TBK1 activates the expression of ISG56 and IFN-β, we also performed luciferase reporter assays in 293T cells. As indicated in FIG. 4B, the expression of TBK1 activated the IFN-β promoter by approximately 90-fold. However, co-expression of $\gamma_1 34.5$ inhibited this induction in a dose dependent manner. Likewise, the $\gamma_1 34.5$ protein suppressed the induction of the ISG56 promoter by TBK1 (FIG. 4C). We conclude that in the absence of any other HSV proteins, the $\gamma_1 34.5$ protein associates with TBK1 and prevents the activation of ISG56 and IFN-β promoters.

Example 5

34.5 Protein is Sufficient to Block Phosphorylation and Nuclear Translocation of IRF3

Figure 5:
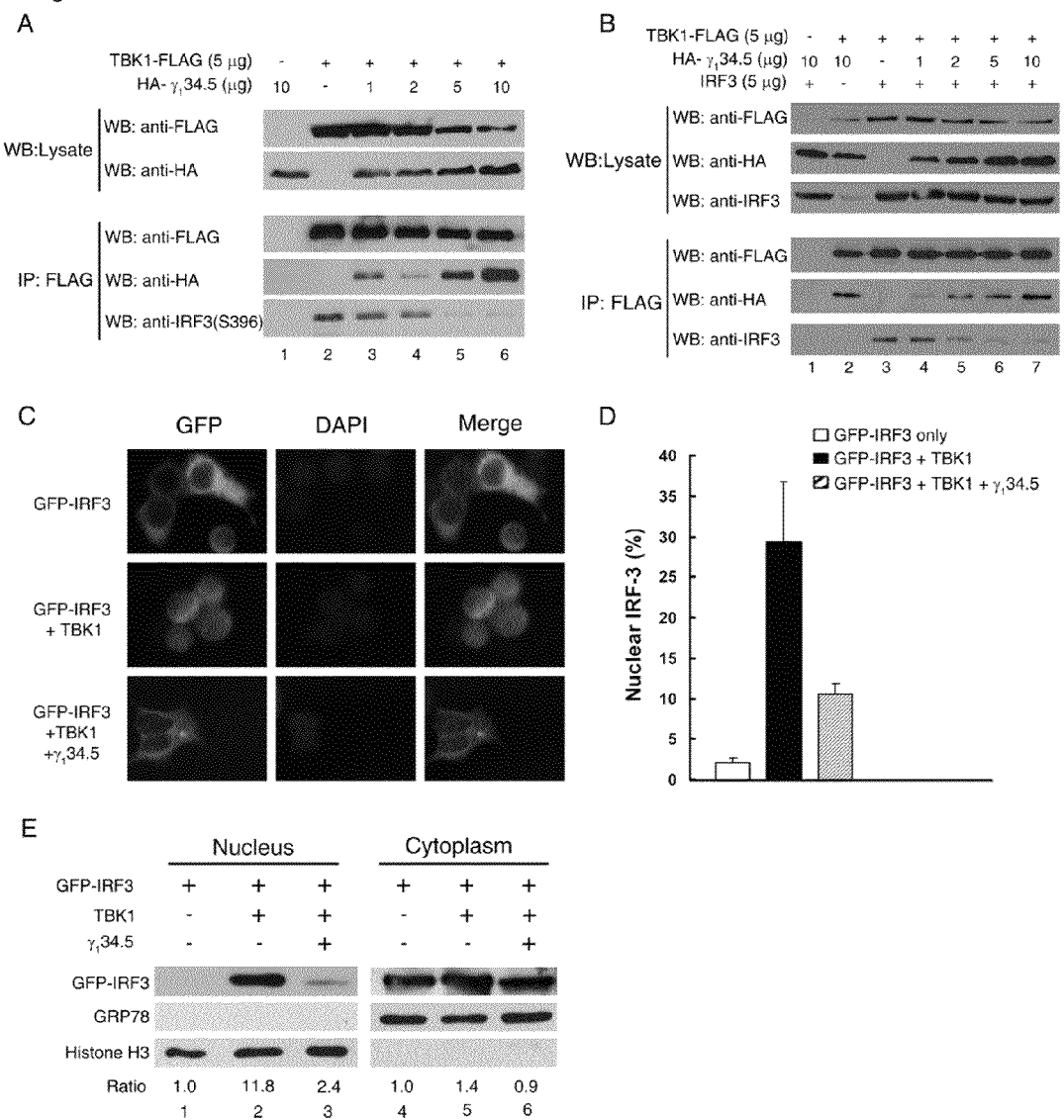
FIG. 5 shows inhibition of TBK1 directed phosphorylation of IRF3 by $\gamma_1 34.5$ protein.

When bound to IRF3, TBK1 phosphorylates the carboxyl terminus of IRF3, which permits nuclear translocation and activation of IRF3 (7,34). To gain insight into $\gamma_1 34.5$ function, we examined whether the $\gamma_1 34.5$ protein directly disrupted this process. Lysates of 293T cells transfected with FLAG-TBK1 and HA-$\gamma_1 34.5$ were immunoprecipitated with anti-FLAG antibody. Immunocomplexes were subjected to in vitro kinase assays with recombinant GST-IRF3 (FIG. 5A). It is notable that there were some variations in TBK1 expression. Nonetheless, as the expression of $\gamma_1 34.5$ was elevated, IRF3 phosphorylation was reduced, indicating that the $\gamma_1 34.5$ protein inhibits IRF3 activation. A simple explanation for the inhibitory effect of the $\gamma_1 34.5$ protein is that it sequesters TBK1 in an inactive complex and blocks the access of IRF3. To test this idea, we analyzed the TBK1 complex by immunoprecipitation. 293T cells were transfected with FLAG-TBK1, IRF3, and HA-$\gamma_1 34.5$. Protein expression was detected in cell lysates (FIG. 5B, upper panels). In parallel, the TBK1 complex was immunoprecipitated with anti-FLAG antibody and subsequently analyzed for the presence of TBK1, $\gamma_1 34.5$, and IRF3 (FIG. 5B, lower panels). Although TBK1 remained at similar levels in immunoprecipitates, IRF3 and $\gamma_1 34.5$ displayed different patterns. In the absence of $\gamma_1 34.5$, IRF3 associated with TBK1 (lane 3). As the level of $\gamma_1 34.5$ increased, the amount of IRF3 associated with TBK1 diminished (lanes 4-7). Thus, expression of the $\gamma_1 34.5$ protein displaced IRF3 in the TBK1 complex. To determine whether $\gamma_1 34.5$ blocked nuclear translocation of IRF3 stimulated by TBK1, a cellular localization experiment was performed in 293T cells expressing GFP-IRF3 or in combination with TBK1 and $\gamma_1 34.5$ (FIG. 5C). When expressed alone, IRF3 remained in the cytoplasm. Addition of TBK1 induced IRF3 redistribution to the nucleus in approximately 30% of GFP-IRF3 positive cells. This response was suppressed to less than 10% upon expression of the $\gamma_1 34.5$ protein as illustrated among cells from different fields (FIG. 5D). Further analysis by cell fractionation revealed similar phenotypes. As illustrated in FIG. 5E, TBK1 strongly stimulated nuclear translocation of GFP-IRF3. However, addition of $\gamma_1 34.5$ drastically reduced nuclear accumulation of GFP-IRF3. Control proteins GRP78 and histone H3 remained in the cytoplasmic and nuclear fractions, respectively. These results suggest that the $\gamma_1 34.5$ protein blocks IRF3 phosphorylation and nuclear translocation.

Example 6

Deletions in the Amino Terminus of 34.5 Disrupt its Activity on TBK1

Figure 6:
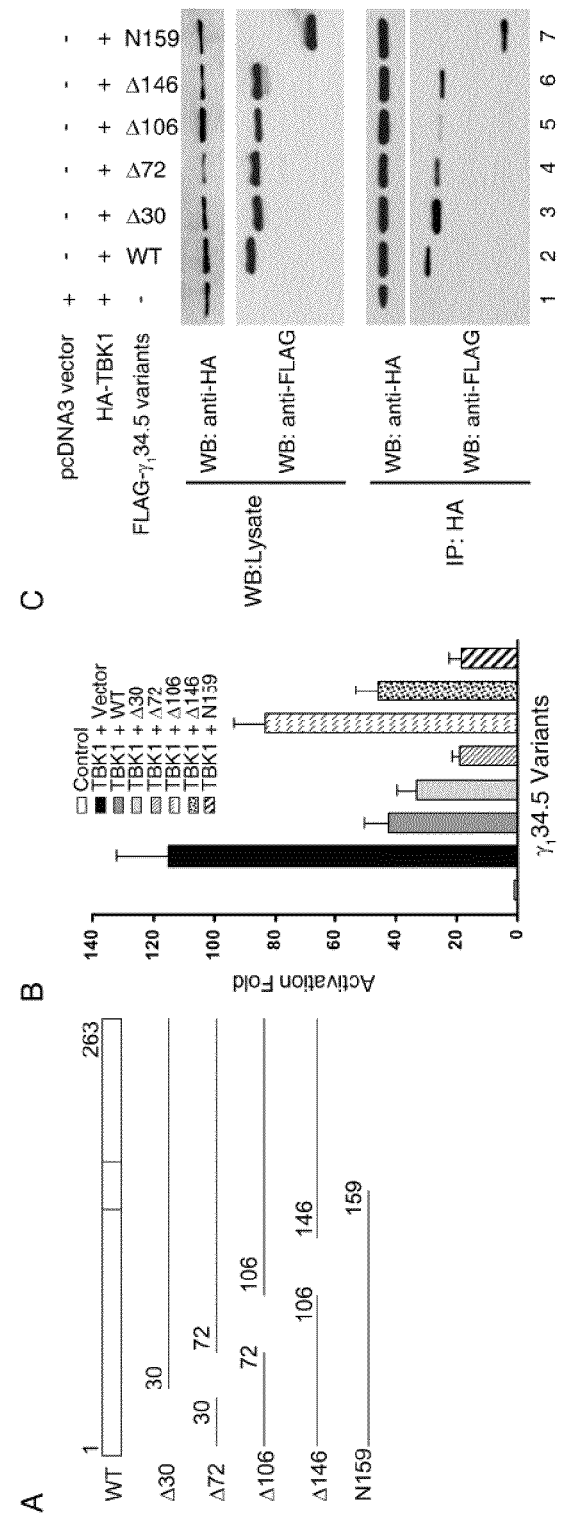
FIG. 6 shows various $\gamma_1 34.5$ protein variants and their ability to bind TBK1.

The $\gamma_1 34.5$ protein consists of 263 amino acids, with a large amino terminal domain, a linker of triplet repeats, and a carboxyl-terminal domain. To map the functional domain, we constructed a series of $\gamma_1 34.5$ variants with deletions in either the amino-terminus or the carboxyl terminus (FIG. 6A). N159 has a deletion in the region spanning amino acids 159 to 263, whereas Δ30, Δ72, Δ106, and Δ146 have deletions in regions encompassing amino acids 1 to 30, 30 to 72, 72 to 106, and 106 to 146, respectively. We first evaluated these mutants in reporter assays with an IFN-β promoter construct (FIG. 6B). Like wild type $\gamma_1 34.5$, N159 suppressed the induction of IFN-β by TBK1 efficiently, indicating that deletion of the carboxyl-terminal domain has no effect. Similarly, Δ30, Δ72, and Δ146 inhibited the IFN-β promoter activity to different degrees. Hence, deletions from amino acids 1 to 72 or from 106 to 146 had little effect on the $\gamma_1 34.5$ activity. In contrast, Δ106 failed to inhibit TBK1 effectively (FIG. 6B). Therefore, deletion of amino acids 72 to 106 in $\gamma_1 34.5$ substantially relieved its inhibitory effect. We next assessed the ability of $\gamma_1 34.5$ to bind TBK1 by immunoprecipitation. As illustrated in FIG. 6C, all $\gamma_1 34.5$ variants, except Δ106, co-precipitated with TBK1. These activities paralleled with the phenotypes seen in reporter assays. These results indicate that the region spanning amino acids 72 to 106 in the $\gamma_1 34.5$ protein is indispensable to inhibit TBK1.

In addition to the foregoing, our data shows that a $\gamma_1 34.5$ N-terminal deletion mutant (lacking amino acids 1-146) is impaired for replication and stimulates interferon expression in cell culture as well as in a mouse model.

Example 7

Materials and Methods Used for Examples 8-13

Mice. BALB/c and C57BL/6 mice were purchased from Harlan Sprague Dawley Inc. and housed under specific pathogen free conditions in biosafety level 2 containment. Groups of five week-old mice were selected for this study. Experiments were performed in accordance with the guideline of the University of Illinois at Chicago.

Cells and viruses. Vero cells were obtained from the American Type Culture Collection and propagated in Dulbecco's modified Eagle's medium supplemented with 10% fetal bovine serum. Myeloid DCs were generated as previously described. Briefly, bone marrow cells were removed from the tibias and femurs of BALB/c mice. Following red blood cell ysis and washing, progenitor cells were plated in RPMI-1640 medium (Invitrogen, Auckland, NZ) supplemented with 10% FBS, 0.1 mM nonessential amino acids, 1 mM sodium pyruvate and 20 ng/ml granulocyte-machrophage colony stimulating factor (GM-CSF, Biosource, Camarillo, Calif.) in 6-well plates at $4 \times 10^6$/well. Cells were supplemented with 2 ml fresh medium every other day. On day 8, DCs were positively selected for surface CD11c expression using magnetic beads (Miltenyi Biotech, Auburn, Calif.) to give >97% pure population of $CD11c^+MHCII^+$ cells. DCs displayed low levels of CD40, CD80, CD86, and major histocompability complex class II (MHC class II) molecules, characteristic of immature DC. Purified $CD11c^+DCs$ were cultured in fresh medium with FBS and GM-CSF and used in subsequent experiments.

HSV-1(F) is a prototype HSV-1 strain used in these studies. In recombinant virus R3616, a 1 kb fragment from the coding region of the $\gamma_1 34.5$ gene was deleted.

Viral infection. Purified $CD11c^+DCs$ were plated in 12 well plates ($5 \times 10^5$ cells/well) and infected with HSV-1(F) or R3616 at indicated multiplicities of infection. After 2 h incubation, cells were washed with phosphate-buffer saline (PBS) and resuspended in RPMI1640 supplemented with 10% FBS and 20 ng/ml GM-CSF. At different time points after infection, cells were harvested for analyses. For in vivo analysis, groups of five mice were anesthetized by intraperitoneal injection of ketamine (100 mg/kg) and xylazine (5 mg/kg). HSV-1(F) or R3616 ($2 \times 10^5$ pfu) was inoculated on the surface of scarified corneas of Balb/C mice bilaterally. On day 1, 3, and 5, whole eyes were collected from sacrificed mice. The corneas were digested with collagenase type I (Invitrogen, Garlsbad, Calif.) at 3 mg/ml for 2 h at 37° C. The digested tissues were passed through a 70-μm nylon cell strainer and spun down at 2000 rpm for 5 min at 4° C. The final pellet was re-suspended in complete RPMI 1640 medium and the single cell suspension was used for further analysis.

RT-PCR analysis. Total RNA from mock infected or virus-infected DCs was extracted using the RNeasy kit (Qiagen Inc. Valencia Calif.). Equal amounts of RNA from each sample were employed to synthesize cDNA using random primers as suggested by manufacturer (Invitrogen, Garlsbad, Calif.). cDNAs were then subjected to PCR amplification for ICP27, UL30, UL44, and 18s rRNA using the specific primers (primers for 18s rRNA were CGCAGCTAGGAATAATGGAA (SEQ ID NO:15) and TTATGACCCGCACTTACTGG (SEQ ID NO:16); primers for ICP27 were CTGGAATCGGACAG-CAGCCGG (SEQ ID NO:17) and GAGGCGCGACCACA-CACTGT (SEQ ID NO:18); primers for UL30 were ACT-AACTTCGACTGGCCCTTC (SEQ ID NO:19) and CCGTACATGTCGATGTTCAAC (SEQ ID NO:20); primers for UL44 were GCCGCCGCCTACTACCC (SEQ ID NO:21) and GCTGCCGCGATCGTGATG (SEQ ID NO:22)). PCR products were separated on a 1.5% agarose gel and visualized with ethidium bromide under ultraviolet light.

Mixed lymphocyte reaction. Spleens were harvested from C57BL/6 mice by cervical dislocation. Single splenocyte suspensions were prepared by forcing tissue through a fine wire mesh using a syringe plunger followed by repeated pipetting in culture medium. After RBC depletion, CD4+ T cells were purified by using the micro-beads (Miltenyi Biotech, Auburn, Calif.) according to the manufacturer's instructions and used as the responder cells. Stimulator cells were bone marrow derived DCs from BALB/c mice and further treated with ultraviolet light before use. The responder cells ($1 \times 10^6$) were labeled with carboxyfluorescein diacetate succinimidyl ester (CFSE, Invitrogen, Garlsbad, Calif.) and co-cultured with the DCs stimulator cells ($2 \times 10^5$) in 2 ml media. After 48 h, proliferation of the responder CD4+ T cells were analyzed using FACS Calibur and data were analyzed by gating of CFSE positive cells with Cell Questpro software (BD).

Flow cytometry. Cells were stained with fluorescein isothiocyanate (FITC) or phycoerythrin (PE)-linked monoclonal antibodies according to the manufacturer's instruction. Briefly, cells were blocked with Fcγ monoclonal antibody (0.5 μg/ml) for 30 min at 4° C. After washing with phosphate buffer saline (PBS), cells were stained with isotype-matched antibodies, anti-CD11c-PE, anti-MHCII-FITC and anti-CD86-FITC antibodies for 30 min on ice with gentle shaking (eBioscience, San Diego, Calif.). Samples were processed and screened using FACS Calibur and data were analyzed with Cell Questpro software (BD).

Flow cytometry of intracellular cytokine production of IL-6, IL-12, IFN-α and IFN-β in cells were performed as follows. Single-cell suspension were stimulated in 96-well plates with anti-CD3 (5 μg/ml) and anti-CD28 (5 μg/ml) mAb for 12 h at 37° C. in 5% CO2, followed by the addition of Monensin (2 μg/ml) for 4 h. After washing two twice with PBS, cells were blocked with 1 μl of Fc mAb (0.5 μg/ml) for 30 min at 4° C. and fixed with 4% of paraformaldehyde at 4° C. for 15 min before permeabilizing with buffer (eBioscience, San Diego, Calif.) at 4° C. for 10 min. After washing once with PBS, cells were stained with appropriate isotype controls, anti-IL-6-FITC, anti-IL-12-FITC, anti-IFN-α-FITC and IFN-β-FITC antibodies (PBL Laboratories, Piscataway, N.J.). Samples were processed and screened using FACS Calibur and data were analyzed with Cell Questpro software (BD).

To determine viral infectivity, DCs mock infected or infected with viruses were fixed in 4% paraformaldehyde (sigma) and permeabilized in permeabilizing buffer (ebioscience, San Diego, Calif.). Cells were blocked with 5% normal mouse serum (sigma), incubated with a monoclonal antibody against HSV-1 ICP27 (Virusys, Sykesville, Md.) and reacted with a goat anti-mouse FITC-conjugated antibody (Santa Cruz biotech, CA). ICP27 expression was determined by flow cytometry.

Interferon bioassay. Culture media from mock infected or virus infected DCs were collected and treated with ultraviolet light to inactivate virus. Where indicated, 30 μg/ml neutralizing antibodies specific to mouse IFNα/β (PBL Laboratories, Piscataway, N.J.) were added to media. Samples were incubated with Vero cells overnight and washed with phosphate-buffer saline. Vero cells were subjected to infection with VSV-GFP (10 pfu/cell). At 10 h after infection, cells were harvested and analyzed by flow cytometry using FACS Calibur and data were analyzed with Cell Questpro software (BD).

Plaque assay. To determine the titer of infectious virus, virus infected DCs were harvested, freeze-thawed three times. Eye tissues were collected from mice and mechanically homogenized. Samples were serially diluted in 199v medium and viral yields were titrated on Vero cells at 37° C.

Immunohistochemistry Analysis. Tissue sections for immunohistochemistry were deparaffinized with xylene and rehydrated through a series of graded ethanols. Endogenous peroxidase activity was quenched using a 0.3% H2O2-methanol bath followed by several washes with phosphate buffered saline. HSV-1 antigens were detected using a 1:1000 dilution of an HSV-1-specific antiserum raised in a rabbit (DAKO) as previously described. Tissue sections were incubated with primary antibody at 43° C. prior to the addition of biotinylated anti-rabbit immunoglobulin secondary antibody, avidin-horseradish peroxidase, and 3,3'-diaminobenzidine tetrahydrochloride (0.04%) in 0.05 M Tris-HCL (pH 7.4) and 0.025% $H_2O_2$ as a chromogen (Ventana Medical Systems, Tucson, Ariz.).

Example 8

HSV-1 Lacking the 34.5 Gene is Capable of Infecting Immature Dendritic Cells (DCs)

Figure 7:
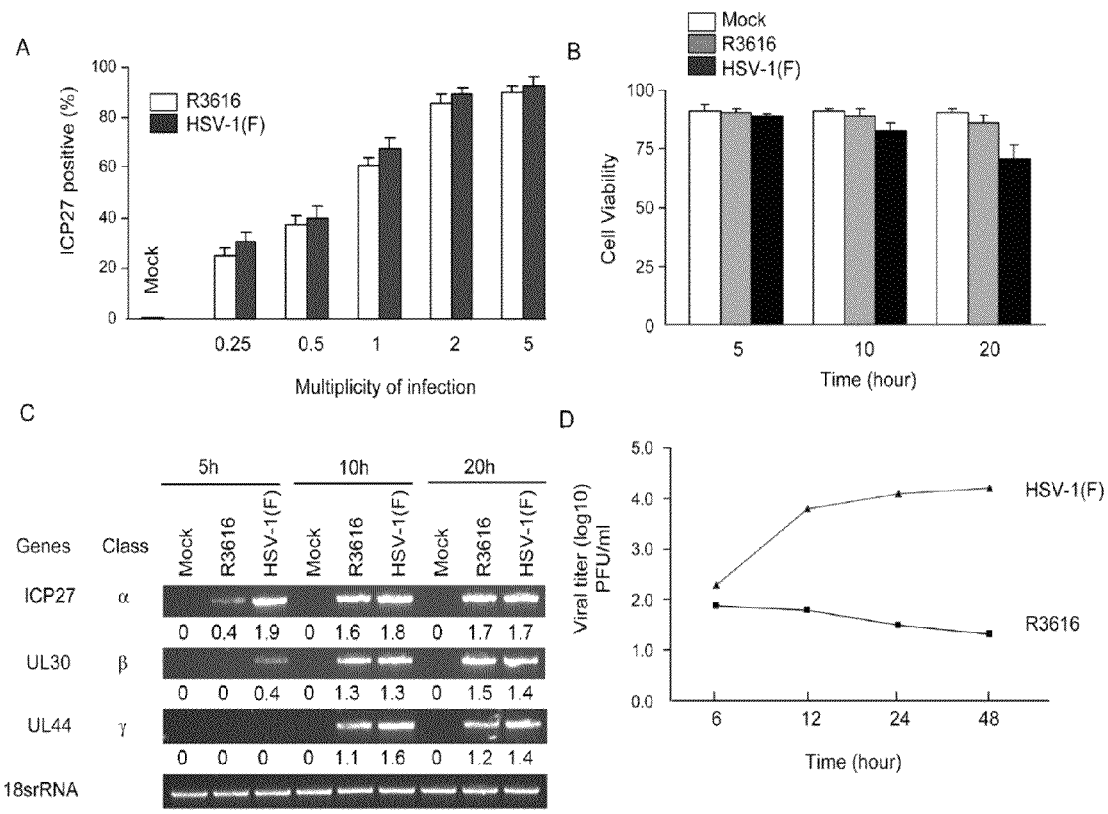
FIG. 7 shows effects of viral infection of immature dendritic cells.

As an initial step, we sought to compare the susceptibilities of DCs to infection with the 34.5 null mutant and wild-type virus. Purified CD11+ DCs were generated from bone marrow in the presence of GM-CSF. These cells, constituting 95% of CD11c+ CD11b+ conventional DCs, were exposed to wild-type HSV-1(F) and R3616 which lacks the $\gamma_1 34.5$ gene. ICP27 expression, as a measure of infectivity, was examined by fluorescence-activated cell sorter analysis. As shown in FIG. 7A, the number of ICP27-positive cells increased in a multiplicity-of-infection-dependent manner. At a multiplicity of infection of 2, more than 85% of cells were positive for ICP27 expression. A higher dose did not increase infectivity. HSV-1(F) and R3616 infected DCs comparably. A cell viability assay showed that at a multiplicity of infection of 2, 90% of DCs infected with R3616 were viable throughout infection (FIG. 7B). A similar result for HSV-1(F)-infected DCs at 5 or 10 h postinfection was seen. There was a slight reduction in the viability of HSV-1(F)-infected cells at 20 h, when 75% of cells were viable.

To assess viral gene expression, total RNA extracted from infected DCs was subjected to RT-PCR amplification (FIG. 7C). At the early time point (5 h), ICP27 expression was detectable in both HSV-1(F)- and R3616-infected cells, but its level was 3.75-fold higher in HSV-1(F)-infected cells. UL30 was expressed only weakly in HSV-1(F)-infected cells, and its level was 3.75-fold lower than that of ICP27. No UL44 was detectable. As virus infection progressed to late time points (10 and 20 h), basically the same levels of ICP27 and UL30 were observed. Levels of UL44 were 14 to 30% higher in HSV-1(F)-infected cells than in R3616-infected cells. We further measured the production of infectious virus in immature DCs infected at 2 PFU per cell. The results presented in FIG. 7D shown that HSV-1(F) replicated to a titer of $6.2\times10^3$ PFU/ml at 12 h postinfection and increased to $1.9\times10^4$ PFU/ml at 48 h postinfection. In contrast, R3616 barely grew, with virus yields remaining at approximately $1.2\times10^2$ PFU/ml over the course of infection. Wild-type virus and the $\gamma_1 34.5$ null mutant were able to infect immature DCs and express viral RNA, but the $\gamma_1 34.5$ null mutant was severely impaired in viral production.

Example 9

34.5 Protein is Required to Suppress HSV-Induced Maturation of Dendritic Cells

Figure 8:
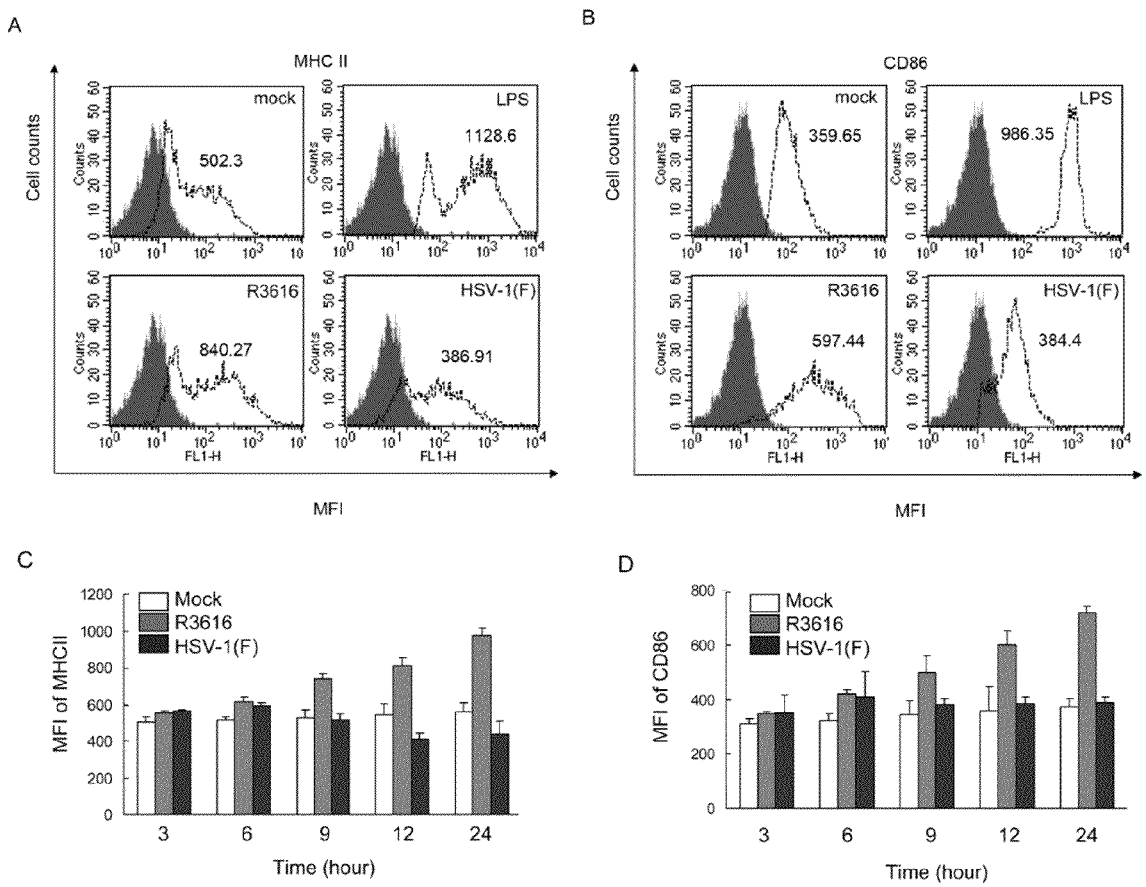
FIG. 8 shows effects of $\gamma_1 34.5$ on the expression of cell surface molecules.

Based on the above-described analysis, we assessed the impact of $\gamma_1 34.5$ on DC maturation. Immature CD11c+ DCs, mock infected or infected with viruses (2 PFU/cell), were subjected to fluorescence-activated cell sorter analysis at 12 h after infection (FIGS. 8A and 8B). We chose to use a multiplicity of infection of 2 because the majority of cells (>85%) are infected and viable after virus infection at this level. As expected, lipopolysaccharide (LPS) induced the up-regulation of MHC-II and CD86 expression compared to that in control mock-infected cells. R3616 also stimulated the expression of MHC-II and CD86, although the magnitude was lower than that for LPS. In contrast, HSV-1(F) reduced the expression of MHC-II slightly and had no stimulatory effect on CD86. To monitor the kinetics of costimulatory-molecule up-regulation, virus-infected DCs were analyzed over a 24-h period. As illustrated in FIGS. 8C and 8D, in HSV-1(F)-infected cells, the expression of MHC-II and CD86 was maintained at basal levels, which were comparable to or slightly lower than those in mock-infected cells at the time points examined. Similar phenotypes in cells infected with R3616 were seen at 3 and 6 h after infection. As infection progressed to 9 h, R3616 stimulated MHC-II and CD86 expression significantly, and expression and further increased at 12 and 24 h after infection. These results suggest that $\gamma_1 34.5$ is required to suppress HSV-induced upregulation of costimulatory molecules in immature DCs.

Figure 9:
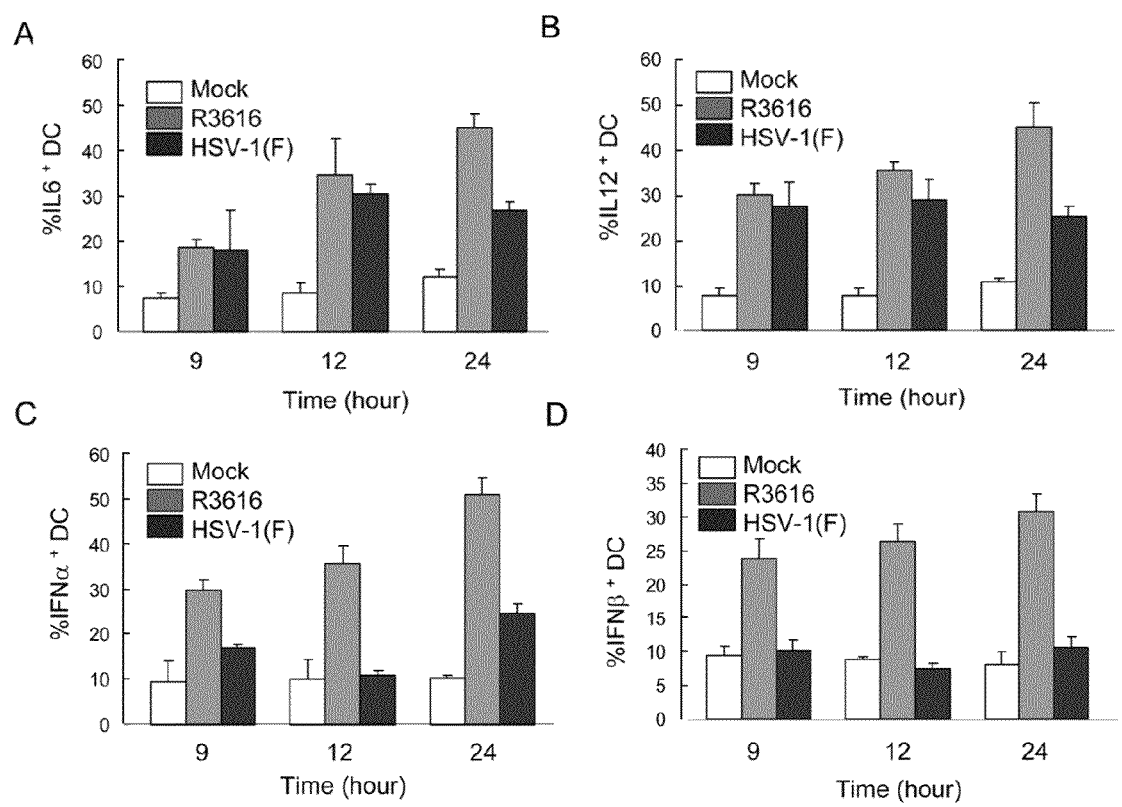
FIG. 9 shows effects of $\gamma_1 34.5$ on cytokine expression

We next analyzed cytokine production by intracellular staining with antibodies against IL-6, IL-12, IFN-α, and IFN-β. As shown in FIGS. 9A and 9B, both HSV-1(F) and R3616 stimulated the expression of IL-6 and IL-12 throughout infection compared to that in mock-infected cells. At 24 h after infection, R3616 induced more cells to produce IL-6 and IL-12 than HSV-1(F). However, the expression patterns for IFN-α and IFN-β were different (FIGS. 9C and 9D). Compared to the proportion among mock-infected cells, HSV-1 (F) infection modestly increased the proportion of IFN-α positive DCs. This effect was not seen for IFN-β positive cells at any of the time points examined. In striking contrast, R3616 infection increased IFN-α and IFN-β-positive cells drastically. Thus, unlike wild-type virus, the $\gamma_1 34.5$ null mutant stimulated IFN-α/β expression in DCs. These results suggest that $\gamma_1 34.5$ is involved in blocking the maturation of DCs during HSV infection.

Example 10

The Interference of 34.5 with Dendritic Cell Maturation is Linked to Reduced IFN Secretion We further evaluated the IFN-α/β secretion among DCs by a bioassay. CD11c+ DCs were mock infected or infected with HSV-1(F) or R3616, and the media were collected and irradiated with UV. The conditioned media, irradiated with UV, were incubated with Vero cells in the presence or absence of neutralizing antibodies against IFN-α/β. Vero cells were then subjected to infection with VSV-GFP, a virus sensitive to IFN. In the this assay, the GFP signal inversely correlates with the IFN level. As revealed by flow cytometry analysis (FIG.

10A), in the absence of neutralizing antibodies against IFN-α/β, only 8.4% of mock-infected or 4.4% of HSV-1(F)-infected cells remained GFP negative. In contrast, 46.3% of R3616-infected cells were GFP negative, indicative of increased IFN secretion. Remarkably, the addition of antibodies against IFN-α/β to R3616-infected cells reduced GFP-negative cells to 6.27%. Neutralizing antibodies had modest effects on cells mock infected or infected with HSV-1(F), which is due likely to a low level of IFN production. We conclude that the $\gamma_1 34.5$ null mutant indeed stimulated IFN-α/β production in DCs and that wild-type virus suppressed IFN-α/β expression.

Figure 10:
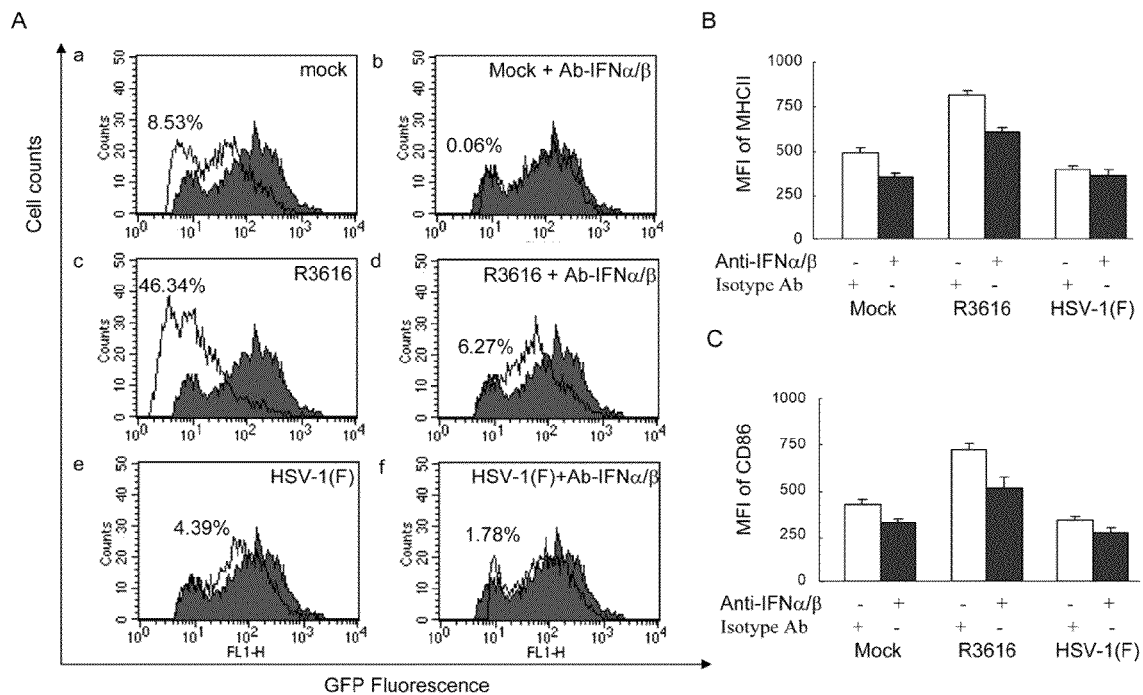
FIG. 10 shows effects of HSV infection on IFN secretion in dendritic cells.

To determine whether IFN secretion was required for DC maturation, DCs, mock infected or infected with viruses, were treated or left untreated with anti-IFN-α/β antibodies. At 12 h after treatment, cells were analyzed for MHC-II and CD86 expression. As shown in FIGS. 10B and 10C, R3616 but not HSV-1(F) stimulated the expression of MHC-II and CD86 in DCs untreated with anti-IFN-α/β. Notably, treatment with anti-IFN-α/β antibodies led to a decrease in MCH-II and CD86 expression when DCs were infected with R3616. This reduction was partial but statistically significant (33%). Treatment with anti-IFN-α/β antibodies had a minor effect on HSV-1(F)-infected or mock-infected cells. Hence, these results suggest that the inhibition of IFN production by $\gamma_1 34.5$ contributes to impaired DC maturation. In addition, $\gamma_1 34.5$ appears to exert its activity independently of IFN production.

Example 11

Figure 11:
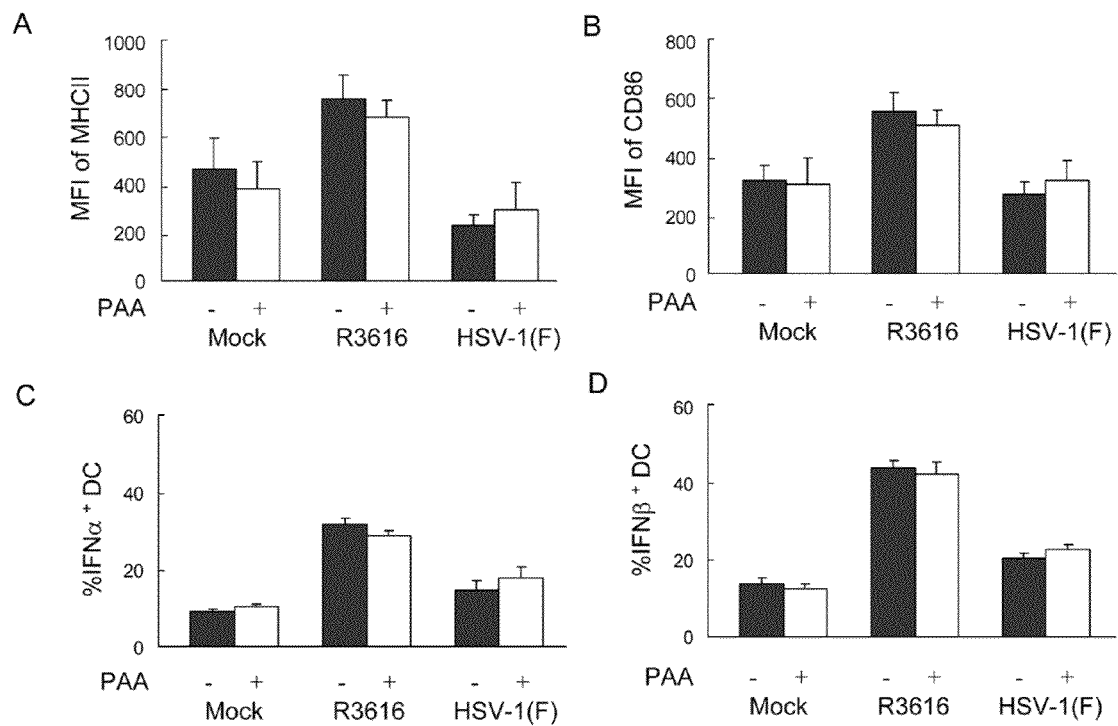
FIG. 11 shows effect of viral DNA replication inhibitor on dendritic cell maturation.

Viral Modulation of Dendritic Cell Maturation is Independent of Viral DNA Replication To test whether viral DNA replication is linked to DC maturation To test whether viral DNA replication is linked to DC maturation, DCs were mock infected or infected with viruses in the presence or absence of PAA (400 μg/ml), a viral DNA polymerase inhibitor. At 12 h post infection, cells were stained for expression of MHC class II, CD86, IFN-α, and IFN-β, respectively. As shown in FIG. 11A, unlike mock infected or HSV-1(F) infected cells, R3616 stimulated MHC class II expression. Similarly, R3616 but not HSV-1(F) stimulated the expression of CD86 (FIG. 11B), IFN-α (FIG. 11C) and IFN-β (FIG. 11D). Notably, these phenotypes were not affected by PAA, an inhibitor of viral DNA replication (data not shown), suggesting that HSV modulation of DC maturation is independent of viral DNA replication.

Example 12

34.5 Protein Attenuates the Capacity of Dendritic Cells to Stimulate T-Cell Activation Because functional DCs stimulate T cell responses, we determined the effect of $\gamma_1 34.5$ on T cell activation. Immature DCs were mock infected or infected with viruses at 2 pfu per cell. At 12 h after infection, cells were treated with UV light to inactivate viruses. In parallel, a set of uninfected cells were stimulated with LPS as a control. The cells were co-cultured with allogeneic CD4+T cells for 48 h and cell proliferation was analyzed by flow cytometry. As shown in FIG. 12A, CD4+T cells alone exhibited 2.2% spontaneous proliferation whereas LPS stimulated a strong proliferation, with 89.72% of CD4+T cells being activated. Mock infected DCs activated T cell proliferation by 47.38%, which represents a background level. Compared to mock infected cells, R3616 infected DCs induced a significantly higher level of T cell proliferation (67.7%). However, wild type HSV-1(F) infected DCs stimulated T cell proliferation weakly (29.25%).

We next measured IFN-γ expression by CD4+ T cells after co-culture with DCs (FIG. 12B). As expected, T cells alone showed a background level of IFN-γ production (0.98%), LPS induced the expression of IFN-γ (53.26%). Similarly, R3616-infected DCs induced a higher percentage of IFN-γ positive T cells (39.35%) than mock-infected DCs (19.88%). However, HSV-1(F) infected DCs induced a background level of IFN-γ13.85%). Together, these results suggest that the $\gamma_1 34.5$ protein is required to inhibit naïve T cells to express IFN-γ and differentiate to Th1 cells by modulating DC maturation.

Example 13

34.5 Protein is Required to Suppress the Maturation of Dendritic Cells In Vivo

Figure 13:
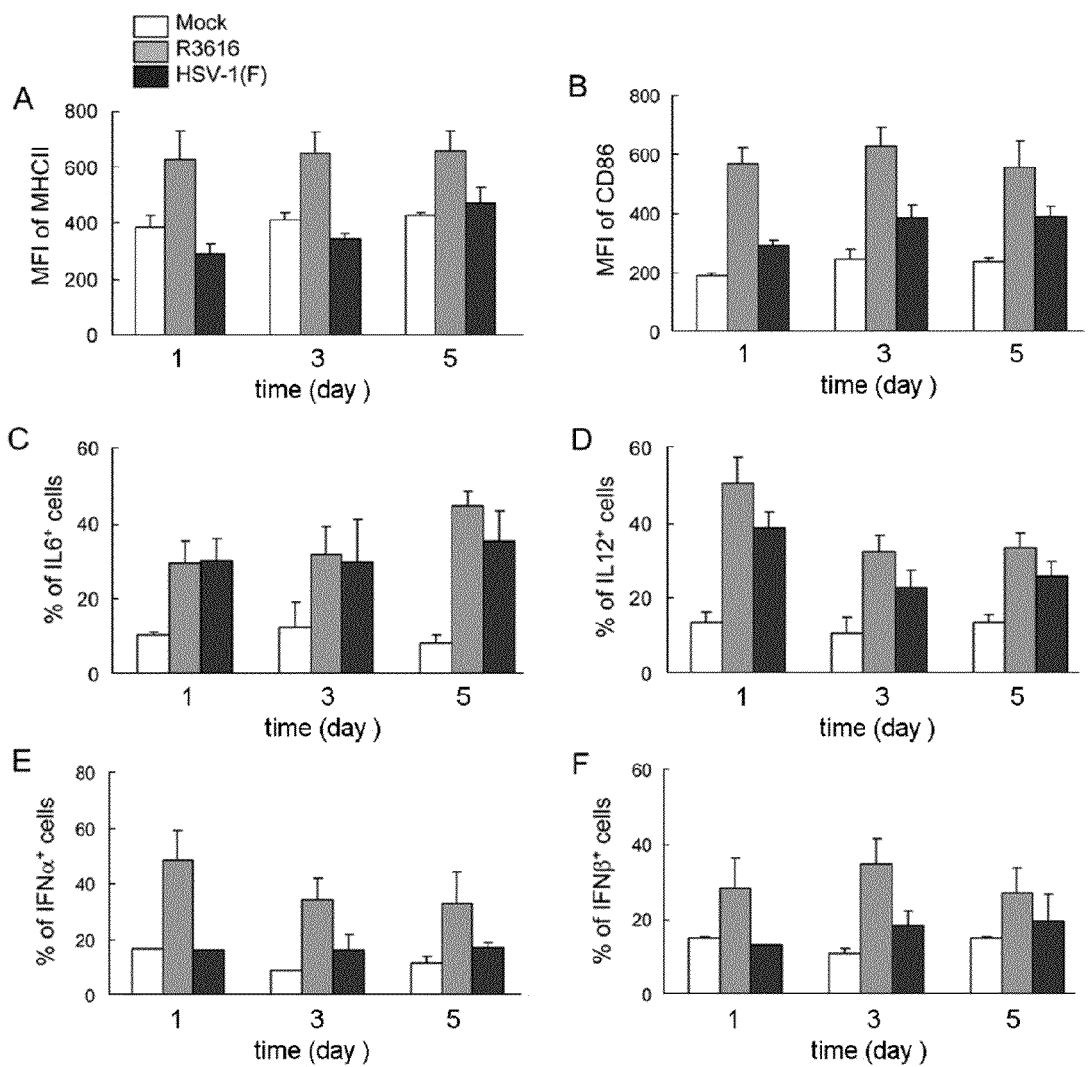
FIG. 13 shows modulation of dendritic cell maturation by $\gamma_1 34.5$ in vivo.

To further examine $\gamma_1 34.5$, we assessed DC maturation in an ocular infection model. Mice were mock infected or infected with viruses ($2\times10^5$ pfu/eye). Single cell suspensions were prepared from the eye tissues after infection and phenotypes of DC11c+ DCs were analyzed by flow cytometry. As depicted in FIGS. 13A and 13B, on day 1, 3, and 5, R3616 consistently stimulated higher levels of MHCII, and CD86 on DCs as compared to mock infection. In contrast, HSV-1(F) expressed lower levels of MHC class 11 and CD86. Thus, the $\gamma_1 34.5$ protein blocked the expression of costimulatory molecules in DCs of infected mice.

Cytokine assays revealed that less than 10% of DCs from mock-infected mice expressed IL-6 and IL-12 on day 1, 3, and 5 (FIGS. 13C and 13D). However, infection with both R3616 and HSV-1(F) resulted in increased number of DCs producing IL-6 and IL-12. Notably, HSV-1(F) induced a slightly less IL-12 over the course of infection. In addition, there was a low level of IFN producing cells (less than 10%) in DCs from mock infected mice (FIGS. 13E and 13F). A similar pattern was seen in DCs from mice infected with HSV-1(F) throughout infection. In contrast, there was a prominent increase in IFN positive DCs from R3616 infected mice, which was evident on day 1 and 3. These results indicate that $\gamma_1 34.5$ is involved in blocking viral induction of type I IFN in DCs in vivo.

Figure 14:
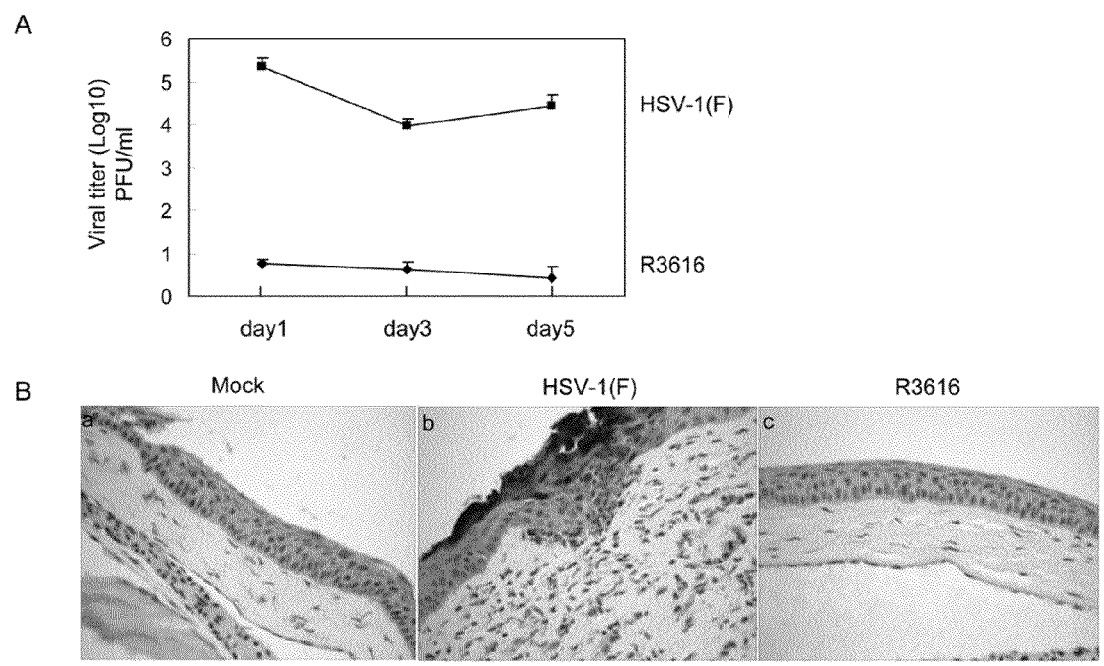
FIG. 14 shows viral replication in the eye.

As a parallel approach, we determined viral replication in the eye. As illustrated in FIG. 14A, HSV-1(F) replicated efficiently in the eye, with titers reaching $5.5\times10^5$ pfu/ml on day 1, $3.9\times10^4$ pfu/ml on day 3, and $4.4\times10^4$ pfu/ml on day 5, respectively. In contrast, R3616 barely replicated over the course of infection. There was a 1000-fold reduction in viral yield as compared to that for HSV-1(F). These phenotypes were also mirrored by immunohistochemistry analysis (FIG. 14B). Viral antigens were only detectable in the eye infected with wild type virus. Thus, viral replication correlated with the inhibition of DC maturation by $\gamma_1 34.5$ in vivo.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

We claim:

1. An attenuated HSV-1 virus comprising a deletion that removes a fragment of only the amino-terminal domain of the $\gamma_1 34.5$ protein, wherein the $\gamma_1 34.5$ protein comprising the deletion is capable of being expressed by the virus, and wherein the $\gamma_1 34.5$ protein does not interact with TBK1.

2. The attenuated HSV-1 virus of claim 1, wherein the deletion is present in at least one copy of a $\gamma_1 34.5$ polynucleotide.

3. The attenuated HSV-1 virus of claim 1, wherein the deletion comprises a fragment selected from the group consisting of amino acid 1 to amino acid 146 of SEQ ID NO: 3 and amino acid 72 to amino acid 106 of SEQ ID NO: 3.

4. An immunogenic composition comprising the virus of claim 1 and an adjuvant.

5. The composition of claim 4, wherein the adjuvant is selected from the group consisting of a sterile oil-in-water emulsion free of animal origin ingredients, wherein the emulsion comprises uniformly dispersed, micron size oil droplets and dimethyldioctadecylammonium bromide; monophosphoryl lipid A (MPL); and Freund.

6. A method of provoking an immune response against a HSV-1 strain in a subject comprising the step of administering to the subject the immunogenic composition of claim 4.

7. The method of claim 6, wherein the subject is human.

8. The attenuated HSV-1 virus of claim 3, wherein the deletion consists of amino acid 72 to amino acid 106 of SEQ ID NO: 3.

9. The attenuated HSV-1 virus of claim 3, wherein the deletion consists of amino acid 1 to amino acid 146 of SEQ ID NO: 3.

* * * * *